United States Patent
Pastine et al.

(10) Patent No.: US 9,631,049 B2
(45) Date of Patent: Apr. 25, 2017

(54) AGENTS FOR REWORKABLE EPOXY RESINS

(75) Inventors: Stefan J. Pastine, San Francisco, CA (US); Bo Liang, Plainsboro, NJ (US); Bing Qin, Minhang District (CN)

(73) Assignee: CONNORA TECHNOLOGIES, INC., Hayward, CA (US)

( * ) Notice: Subject to any disclaimer, the term of this patent is extended or adjusted under 35 U.S.C. 154(b) by 270 days.

(21) Appl. No.: 13/988,817

(22) PCT Filed: Jul. 8, 2011

(86) PCT No.: PCT/CN2011/076980
§ 371 (c)(1),
(2), (4) Date: May 22, 2013

(87) PCT Pub. No.: WO2012/071896
PCT Pub. Date: Jun. 7, 2012

(65) Prior Publication Data
US 2013/0245204 A1    Sep. 19, 2013

Related U.S. Application Data

(60) Provisional application No. 61/344,962, filed on Nov. 30, 2010.

(51) Int. Cl.
| | |
|---|---|
| C08G 59/66 | (2006.01) |
| C07D 295/13 | (2006.01) |
| C07D 317/08 | (2006.01) |
| C07C 217/08 | (2006.01) |
| C07C 217/84 | (2006.01) |
| C07C 323/12 | (2006.01) |
| C08G 59/50 | (2006.01) |
| C08G 59/40 | (2006.01) |
| C08L 63/00 | (2006.01) |

(52) U.S. Cl.
CPC ............ *C08G 59/66* (2013.01); *C07C 217/08* (2013.01); *C07C 217/84* (2013.01); *C07C 323/12* (2013.01); *C07D 295/13* (2013.01); *C07D 317/08* (2013.01); *C08G 59/4064* (2013.01); *C08G 59/50* (2013.01); *C08G 59/504* (2013.01); *C08L 63/00* (2013.01)

(58) Field of Classification Search
CPC ................................. C08L 63/00; C08G 59/66
USPC ........................................................ 525/409
See application file for complete search history.

(56) References Cited

U.S. PATENT DOCUMENTS

| | | | |
|---|---|---|---|
| 3,786,029 A | | 1/1974 | Bechara |
| 3,879,465 A | * | 4/1975 | Bechara ............... C08G 59/504 521/129 |
| 4,136,092 A | * | 1/1979 | Jackle .................. C07D 251/50 528/28 |
| 4,177,173 A | * | 12/1979 | Carr ............................... 528/88 |
| 4,581,423 A | * | 4/1986 | Speranza et al. ............ 525/504 |
| 4,820,743 A | * | 4/1989 | Ishikawa ................ C08G 18/63 521/137 |
| 5,191,015 A | * | 3/1993 | Sheppard ............... C07K 1/042 525/54.1 |
| 5,310,789 A | * | 5/1994 | Furihata ................ C08G 59/50 525/113 |
| 5,891,367 A | * | 4/1999 | Basheer ............... C08G 59/504 252/514 |
| 5,932,682 A | | 8/1999 | Buchwalter et al. |
| 2005/0234216 A1 | * | 10/2005 | Klein et al. ................... 528/422 |
| 2009/0192265 A1 | * | 7/2009 | Hasegawa et al. ........... 525/101 |
| 2010/0184890 A1 | * | 7/2010 | Constantinescu ....... C07C 41/03 524/101 |
| 2011/0244245 A1 | * | 10/2011 | Elgimiabi ..................... 428/416 |
| 2012/0012505 A1 | * | 1/2012 | Compton ............... C10G 29/20 208/207 |
| 2014/0221510 A1 | * | 8/2014 | Liang et al. .................... 521/40 |
| 2014/0357802 A1 | * | 12/2014 | Aou et al. ................. 525/329.3 |
| 2015/0050659 A1 | * | 2/2015 | Sebo .................... C07F 9/65586 435/6.12 |

FOREIGN PATENT DOCUMENTS

| | | |
|---|---|---|
| GB | 846377 | 8/1960 |
| JP | 1225635 | 9/1989 |
| WO | 2009126933 | 10/2009 |

OTHER PUBLICATIONS

Written Opinion for International Patent Application No. PCT/CN2011/076980, dated Oct. 13, 2011, 6 pages.
International Search Report for International Patent APplication No. PCT/CN2011/076980, dated Oct. 13, 2011, 6 pages.
International Preliminary Report on Patentability for International Patent Application No. PCT/CN2011/076980, dated Jun. 13, 2013, 2 pages.

* cited by examiner

*Primary Examiner* — Megan McCulley
(74) *Attorney, Agent, or Firm* — Lando & Anastasi, LLP

(57) ABSTRACT

Compounds of formula I, uses as crosslinking agents or curing agents thereof, and resins obtained by using the compounds as crosslinking agents.

22 Claims, No Drawings

AGENTS FOR REWORKABLE EPOXY RESINS

CROSS-REFERENCE TO RELATED APPLICATION

This application is a U.S. national stage entry of International Patent Application No. PCT/CN2011/076980, filed 8 Jul. 2011, which in turn claims priority to and benefit of U.S. Provisional Application No. 61/344,962, filed on Nov. 30, 2010, the contents of which are incorporated herein by reference in their entireties.

BACKGROUND OF THE INVENTION

Epoxies are an important class of thermosetting polymers. They have diverse applications including adhesives, structural materials, paints coatings, potting, printed circuit boards, microelectronic encapsulation, the aerospace industry, and other consumer goods. Epoxy resins are hardened or cured by a cross-linking reaction using one of three methods. The chemistry of epoxy curing is explained in great detail in the Handbook of Composites (edited by S. T. Peters, Chapter 3, pp 48-74, published by Chapman & Hall, 1998). The properties and applications of cured resin are greatly influenced by the choice of the hardener formulation or the method of curing.

One method is simply the reaction of the epoxy resin with itself (i.e. homopolymerization) via a ring-opening polymerization mechanism of the epoxy groups. The self-curing of epoxy resins usually requires an elevated temperature but can be initiated with either a Lewis acid or a Lewis base catalyst (as opposed to a curing agent).

In the second method, the epoxy resin is cured with a cyclic acid anhydride. The anhydride can react with the epoxy group, pendant hydroxyls, or residual water to form a carboxylate intermediate, which then reacts with the epoxy group, causing a self-perpetuating reaction between the anhydride and the epoxy resin. Catalytic amounts of tertiary amines are commonly used as additives as they facilitate the opening of the anhydride. Anhydride epoxy formulations do not readily cure at room temperature, and generally require a significant room temperature of 80-150° C.

In the third method, the epoxy resin reacts in the ambient with polyvalent nucleophiles such as polyamines to form a polymeric network of essentially infinite molecular weight. Polyamines of the general formula ($NH_2$—R—$NH_2$) give cold curing compositions. The ring opening of the epoxy ring with a primary or secondary amine generates a stable C—N bond. Epoxy groups will react with potentially every amine containing an active hydrogen atom, so that a simple diamine ($NH_2$—R—$NH_2$) acts as a tetrafucntional crosslinker and reacts with four epoxy groups. Similar to amines, polythiol compounds (HS—R—SH) also react with epoxy rings to form C—S bonds. The reaction of the thiol group with the epoxy group is greatly facilitated by the presence of a catalytic amount of base, such as a tertiary amine. A simple dithiol compound (HS—R—SH) serves only as difucntional chain extender since a primary thiol contains only one active hydrogen atom, but polythiol compounds with a functionality greater than three serve as cross-linkers. Polythiol hardeners also allow for ambient curing compositions. Faster setting formulations, which are commonly sold as two-pack glues in hardware stores, usually contain polythiol hardeners or both polythiol and polyamine hardeners.

By far, the most common epoxy formulations consist of a diepoxide ("resin") and a polyamine ("hardener") to form a polymeric network of essentially infinite molecular weight. The combination of "resin and hardener" is sometimes referred to as "cured epoxy," "cured resin," or simply "resin" or "epoxy." The widespread utility of such epoxy formulations is due to their excellent processability prior to curing and their excellent post-cure adhesion, mechanical strength, thermal profile, electronic properties, chemical resistance, etc. Furthermore, the high-density, infusible three-dimensional network of epoxies makes it an extremely robust material, resulting in it being the material of choice for many long-term applications. At the same time, this durability makes its removal, recycling and reworkability notoriously difficult, raising concerns about the longevity of epoxy-based materials in the environment. The cross-linking reactions that occur with two convertibly used component epoxies are essentially irreversible. Therefore, the material cannot be melted and reshaped without decomposition of the material. The ordinary consumer is also aware of the intractability of epoxy adhesives and coatings; internet message boards are replete with postings and complaints on how to remove epoxy that has spilled on unwanted places or mistakenly bonded items together. Thus, there exists a need for new epoxy formulations that retain the remarkable physical properties of classical epoxies, but can be disassembled in a controlled and mild manner when desired, without damaging the underlying structure.

As epoxy adhesives are used for the assembly of a variety of common items and epoxies serve as the matrix materials for a variety of structural materials and composites, the development of such a "reworkable" material would have implications in recycling, recovery, and waste disposal. Furthermore, an easily removable epoxy could expand the use of epoxies to new consumer markets. For example, joints could be bonded with epoxy glue and any spill-over could be easily removed, even post-curing, while the joint remains bonded. As another example, epoxy based paints and varnishes could be more easily removed.

The intractability of a cured resin stems, in part, from its highly cross-linked network. If the links in the three-dimensional network can be cleaved under controlled conditions, the network can be disassembled into smaller, soluble molecules and/or polymer, therefore removing the cured resin stem. In principal, this can be accomplished through use of either a dissolvable resin or a curing agent that contains a bond capable of cleavage under a specific set of conditions. In the limited amount of prior art on this topic, the majority has focused on cleavable groups in the resin component. Epoxy formulations that possess cleavable linkages in the hardener, are particularly attractive, as those skilled in the art realize that a great deal of more flexibility exists with regard to the constituents in a hardener component, due to the resin components in most epoxies are based on bisphenol digylcidly ether (BPADGE).

U.S. Pat. No. 5,932,682 discloses the use of diepoxide resins that contain ketal or acetal linkages for use as removable electronic encapsulation. The anhydride cured resins were shown to disassemble in acid at an elevated temperature. There are no examples of curing the resins with polyamine, polythiols, or acid liable hardeners. Further, the use of acid-sensitive linkages in the hardener component, or both hardener and resin, has not been previously documented or considered to those skilled in the art.

SUMMARY OF THE INVENTION

In one aspect, the present invention provides a new class of cross-linking agents or hardeners useful for preparing cross-linked polymers or curing resins. These crosslinking agents are of Formula I shown below:

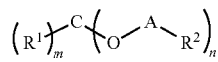

In Formula I,
m is 2, 1, or 0;
n is 2, 3, or 4;
the sum of m and n is 4;
each $R^1$ is independently hydrogen, alkyl, cylcoalkyl, heterocycle, heterocycloalkyl, alkenyl, cycloalkenyl, aryl, heteroaryl, alkoxyalkyl, or alkynyl; each A is independently alkyl, alkylene, alkenene, alkylene-hetero-alkylene, alkylene-heterocyclo-alkylene, carbonyl, thiocarbonyl, alkylene-oxy-alkylene, 1,4-alkyl substituted piperazine, aryl, or heteroaryl;
each $R^2$ is independently —$NHR^3$,—SH, or heterocycloalkyl, wherein each $R^3$ is independently hydrogen, alkyl, aminoalkyl, alkylaminoalkyl, cylcoalkyl, heterocycle, alkenyl, aryl, or heteroaryl;
or, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group.
In some embodiments, each $R^1$ is independently hydrogen, $C_{1-12}$ alkyl (e.g., $C_{1-6}$ alkyl), $C_{3-12}$ cycloalkyl (e.g., $C_{4-6}$ cycloalkyl), $C_{6-12}$ aryl (e.g., $C_{6-10}$ aryl), or $C_{3-11}$ heteroaryl (e.g., $C_{3-8}$ heteroaryl). Specific examples of $R^2$ include, but are not limited to, hydrogen, methyl, ethyl, propyl, 2-proptyl, butyl, 2-butyl, or t-butyl.
In some other embodiments, each $R^2$ is independently —$NHR^3$, —SH, or 4- to 10-membered heterocycloalkyl, wherein each $R^3$ is independently hydrogen, alkyl (e.g., $C_{1-8}$ alkyl), cycloalkyl, heterocycle, aryl, or heteroaryl, each 4- to 10-membered heterocycloalkyl contains at least one ring nitrogen atom and is optionally substituted at a ring carbon atom with at least one amino or thiol group. Specific examples of $R^2$ include, but are not limited to, —$NHR^3$, —SH, or 4-piperazinyl, and specific examples of $R^3$ include, but are not limited to hydrogen, methyl, or ethyl.
In some other embodiments, each A is independently $C_{1-8}$ alkylene, $C_{2-12}$ alkylene-hetero-alkylene, $C_{4-16}$ alkylene-heterocyclo-alkylene, aryl, carbonyl, or thiocarbonyl. For instance, each A can be a $C_{1-8}$ alkylene, $C_{1-8}$ alkylene-hetero-alkylene, $C_{4-10}$ alkylene-heterocyclo-alkylene, or benzene. Specific examples of A include, but are not limited to, ethylene, propylene, isopropylene, butylene, iso-butylene, hexylene, ethylene-oxy-ethylene, ethylene-amino-ethylene,

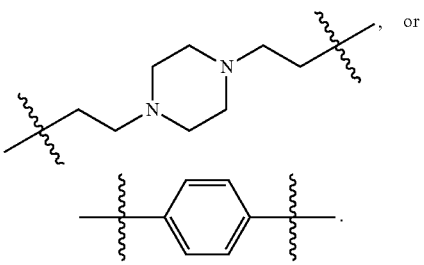

In some other embodiments, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group. Specifically, every two —O-A-R2 groups, together with the carbon atom to which they are attached to, can independently form an 1,3-dioxane substituted st the ring carbon atom with at least an aminoalkyl group. More specific examples include, but are not limited, two —O-A-R2 groups, together with the carbon to which they are attached to, independently form

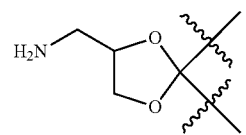

In still some other embodiments, m is 2 and n is 2; m is 1 and n is 3; or m is 0 and n is 4.

In still further embodiments, the compound of Formula I is

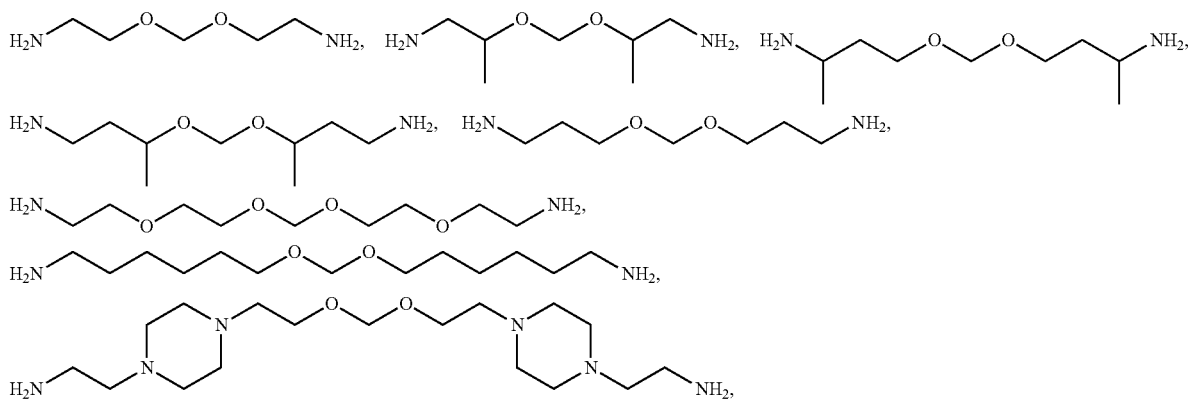

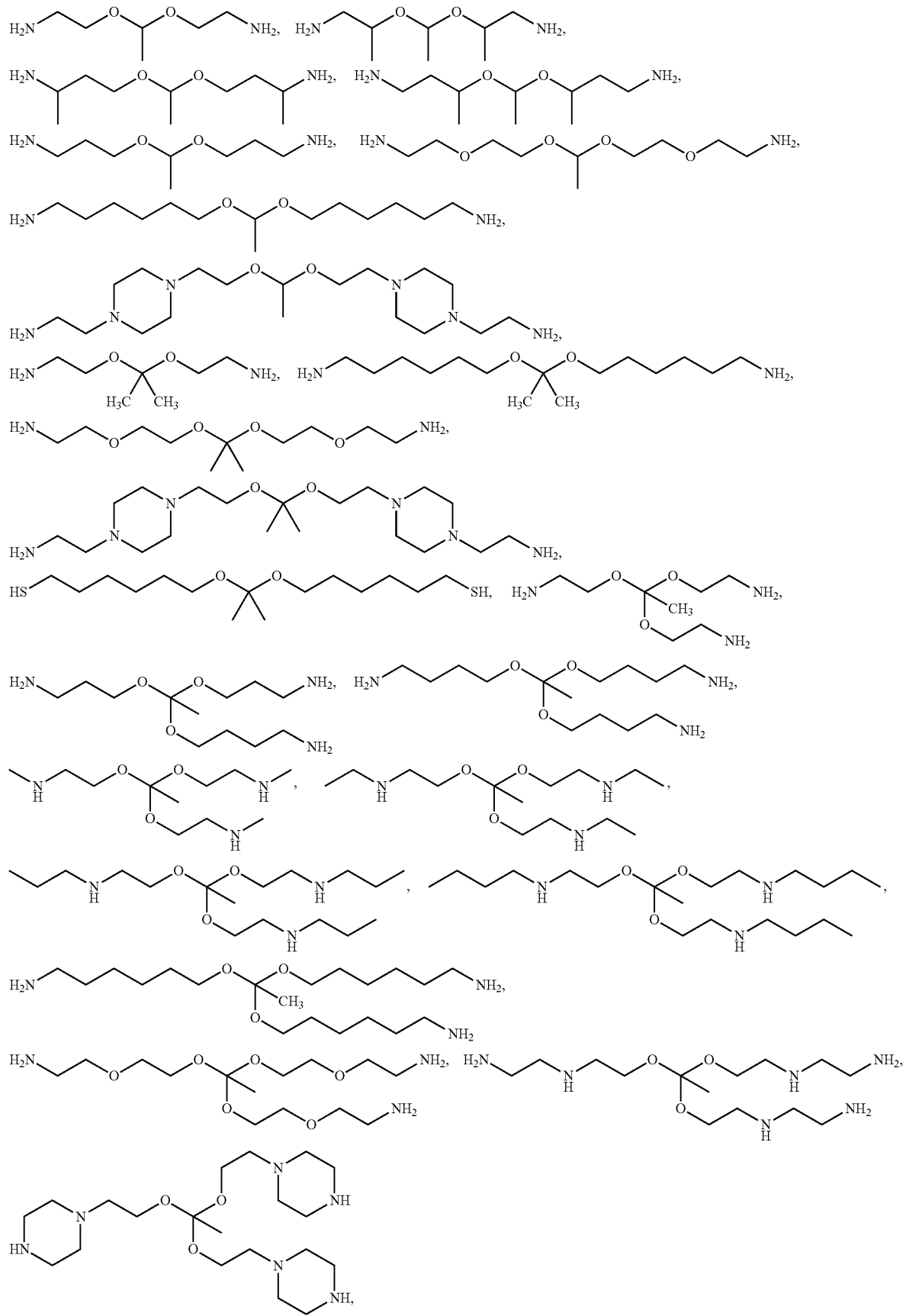

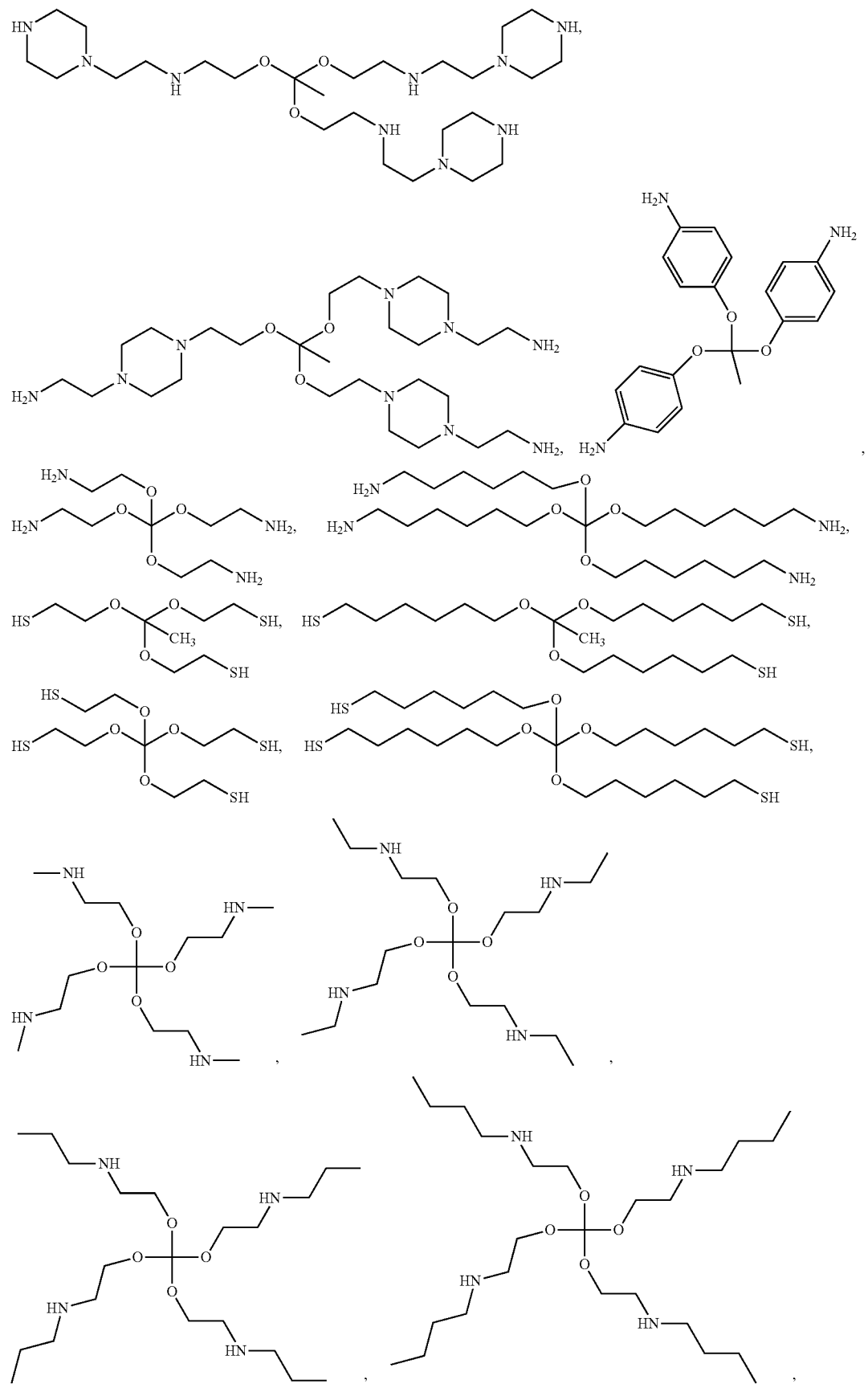

-continued
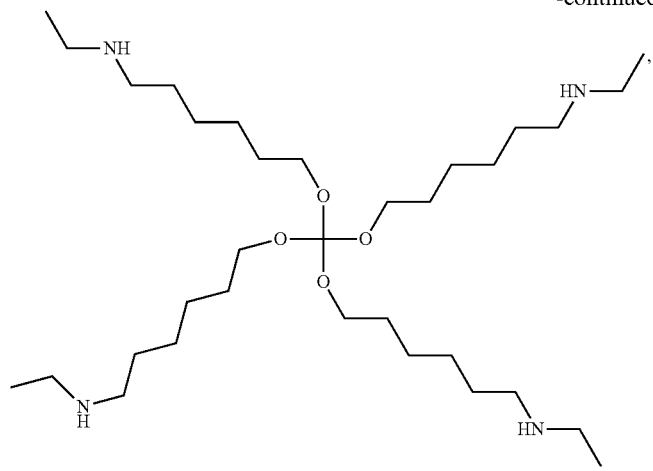
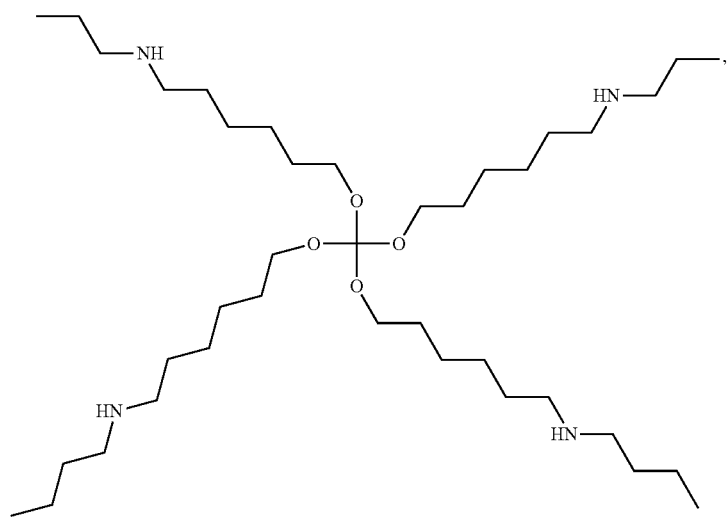
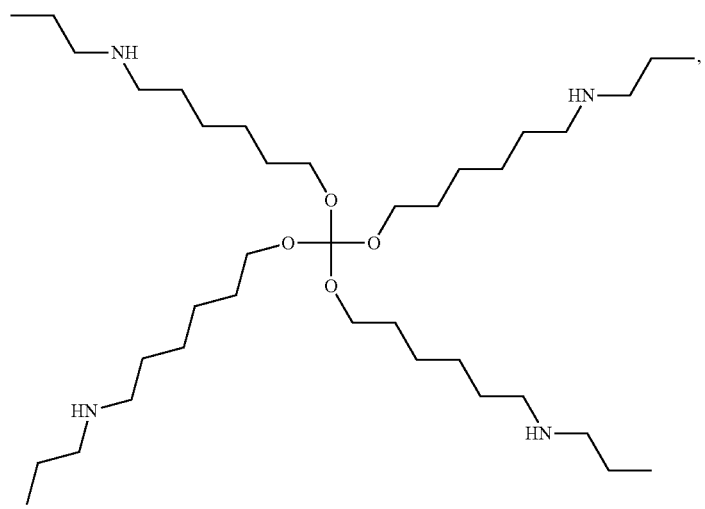

-continued
11
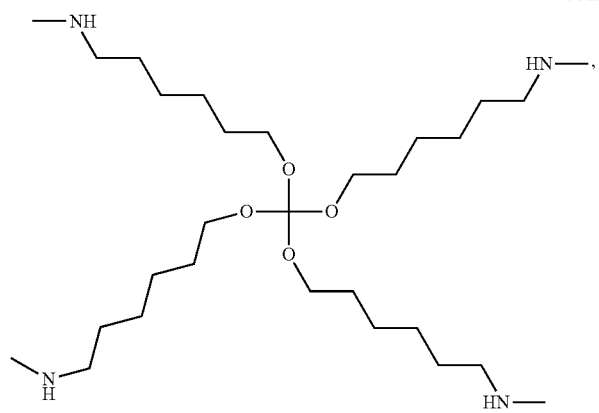
12
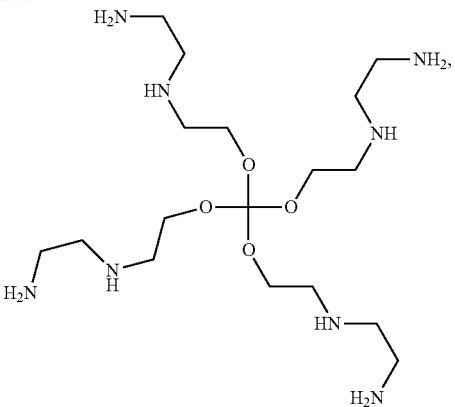
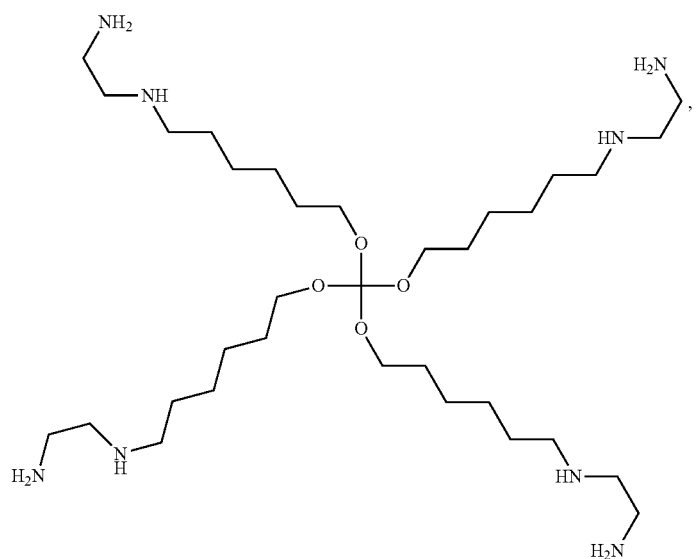
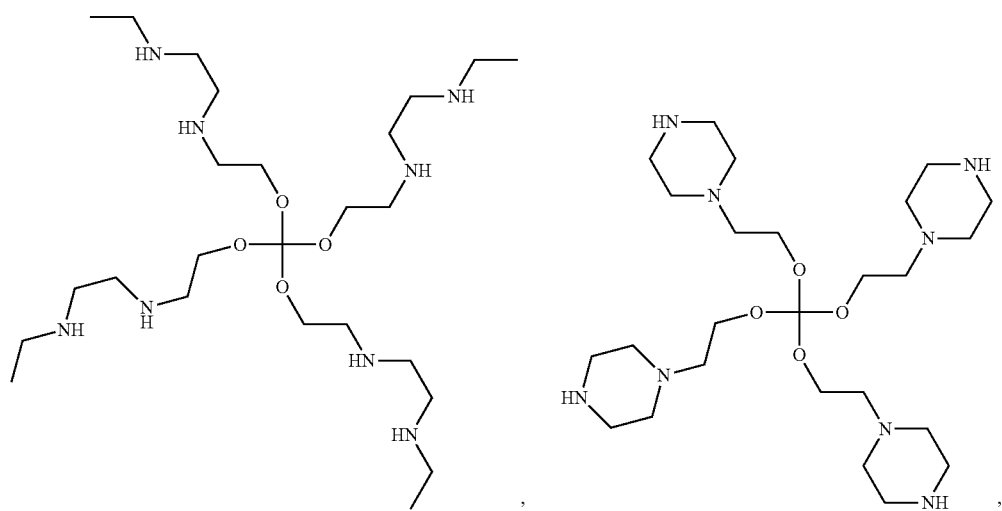

-continued
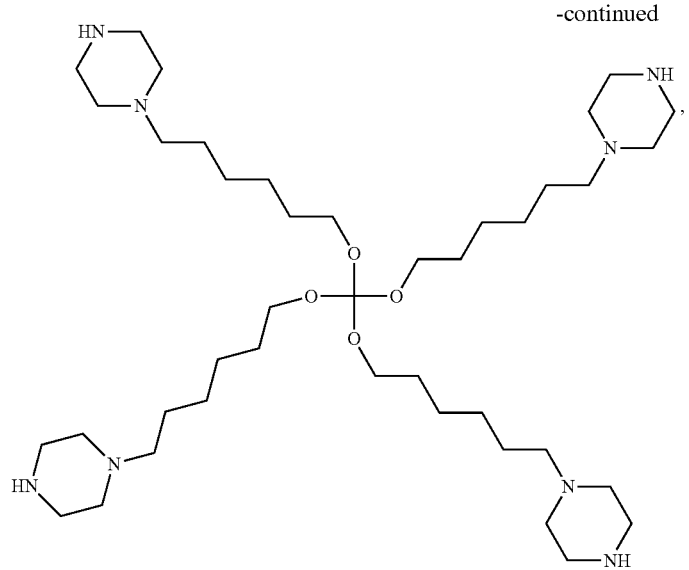
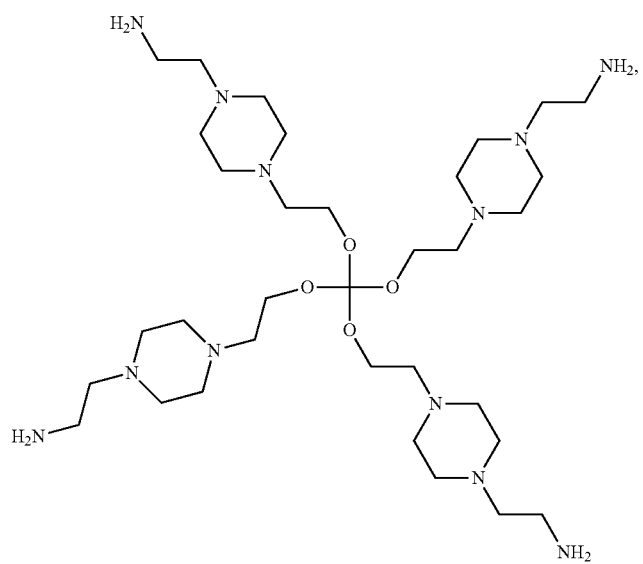
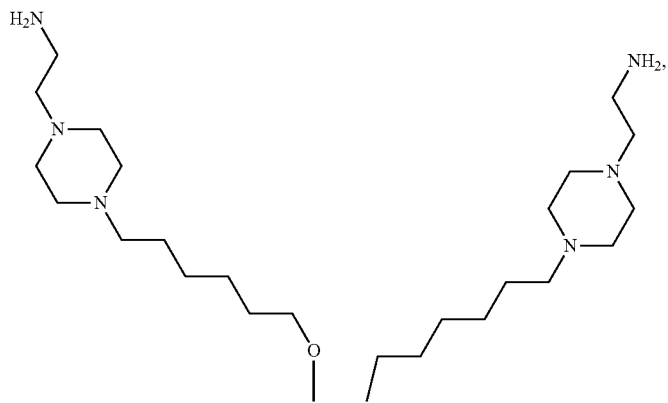

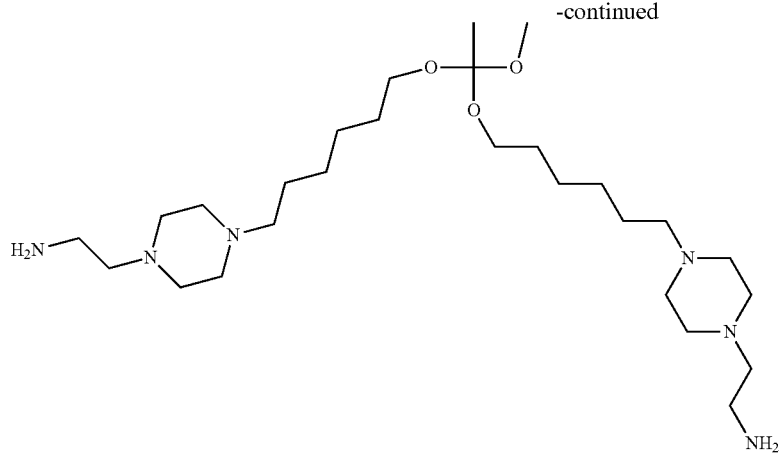

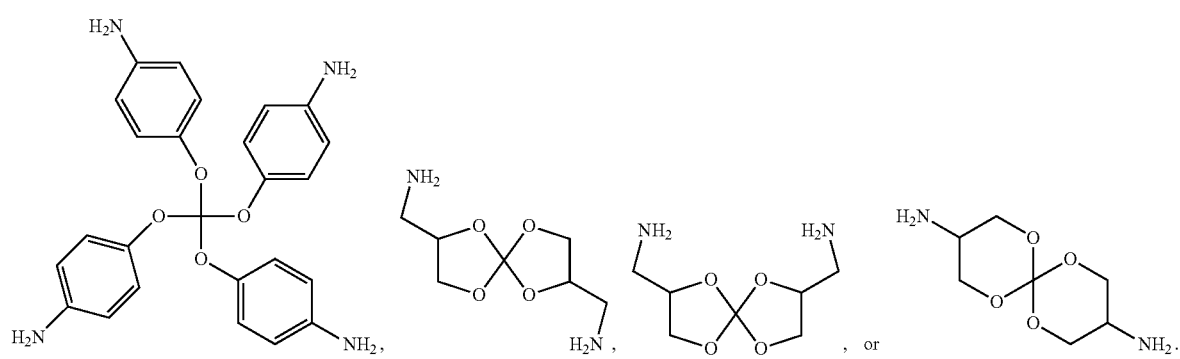

Another aspect of this invention provides cross-linked polymers each comprising a cross-linking group of Formula II:

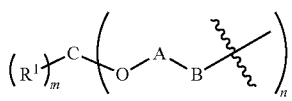

In Formula II,
m is 2, 1, or 0;
n is 2, 3, or 4;
the sum of m and n is 4;
each $R^1$ is independently hydrogen, alkyl, cycloalkyl, heterocycloalkyl, alkenyl, cycloalkenyl, aryl, heteroaryl, alkoxyalkyl, or alkynyl;
each A is independently alkyl, alkenene, alkylene-heteroalkylene, alkylene-heterocyclo-alkylene, alkylene, carbonyl, thiocarbonyl, alkylene-oxy-alkyene, 1,4-alkyl substituted piperazine, aryl, or heteroaryl;
each B is independently —$NR^3$—, 1-alkylpiperazine, —S—, or heterocycloalkyl, wherein each $R^3$ is independently hydrogen, alkyl, cyclcoalkyl, heterocycle, alkenyl, aryl, or heteroaryl;
or, every two —O-A-B groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino.

In some embodiments, every two —O-A-B groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino.

In some embodiments, each B is independently connected through one or two covalent bonds to one or two independent substituted 2-hydroxyethyl groups. Examples of the substituted 2-hydroxyethyl group include 1-(4-(2-(4-(oxiran-2-ylmethoxy)phenyl)propan-2-yl)phenoxy)propan-2-ol-3-yl group or its derivatives. Examples of the derivatives of 1-(4-(2-(4-(oxiran-2-ylmethoxy)phenyl)propan-2-yl)phenoxy)propan-2-ol-3-yl group include those in which the oxiranyl moiety is opened by a ring-opening reaction, e.g., to give a terminal hydroxyl group.

In some other embodiments, each B is independently —$NR^3$— or —S—, wherein each $R^3$ is independently a bond, hydrogen, or $C_{1-6}$ alkyl.

In still some other embodiments, two B moieties in a single cross-linking group of Formula II can be connected through bonds to a common bridge.

In yet still some other embodiments, one respective B moiety in two cross-linking groups of Formula II is connected to a common bridge.

In still another aspect, the invention provides a method for preparing a compound of Formula I:

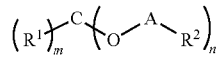

wherein:
m is 2, 1, or 0;
n is 2, 3, or 4;
the sum of m and n is 4;
each $R^1$ is independently hydrogen, alkyl, cycloalkyl, heterocycle, alkenyl, cycloalkenyl, alkynyl, aryl, or heteroaryl;
each A is independently alkyl, alkenene, alkylene-heteroalkylene, alkylene-heterocyclo-alkylene, alkylene, carbonyl, thiocarbonyl, aryl, heteroaryl, heterocycle, or polyether;
each $R^2$ is independently —$NHR^3$, —SH, or heterocycloalkyl, wherein each $R^3$ is independently hydrogen, alkyl, cylcoalkyl, heterocycle, alkenyl, aryl, heteroaryl, or heterocycle;
or, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group.

In some embodiments, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group. The method includes reacting an orthoketone, dialkoxyalkane, orthoester, or orthocarbonate with an aminoalcohol, haloalcohol, mercaptoalcohol, or any alcohol with a leaving group.

In some embodiments, each $R^2$ is independently —$NHR^3$ and each $R^3$ is independently hydrogen, alkyl, alkenyl, aryl, heteroaryl, or heterocycle.

In some other embodiments, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group.

In some other embodiments, the method comprises reacting an orthoketone, dialkoxyalkane, orthoester, or orthocarbonate with an aminoalcohol or halogen alcohol to give an intermediary compound. For instance, the orthoester can be trialkoxyalkane, and the orthocarbonate can be tetraalkoxyalkane.

In some other embodiments, the dialkoxyalkane is dialkoxypropane; the orthoester is trialkyl orthoacetate; and the orthocarbonate is tetraalkyl orthocarbonate.

In still some other embodiments, the method further includes reacting the intermediary compound with hydrazine to give the compound of Formula I.

In some other embodiments of the method, each $R^2$ is independently —SH.

In yet some other embodiments, the method further comprises reacting an orthoester, orthoketone, or orthocarbonate with a mercaptoalcohol.

As used herein, the term "alkyl," when used alone or as part of a larger moiety (e.g., as in "cycloalkenylalkyl" or "haloalkyloxy"), refers to a saturated aliphatic hydrocarbon group. It can contain 1 to 12 (e.g., 1 to 8, 1 to 6, or 1 to 4) carbon atoms. As a moiety, it can be denoted as —$C_nH_{2n+1}$. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, and 2-ethylhexyl. An alkyl group can be substituted (i.e., optionally substituted) with one or more substituents. When an alkyl is preceded by a carbon-number modifier, e.g., $C_{1-8}$, its means the alkyl group contains 1 to 8 carbon atoms.

As used herein, the term "alkylene," when used alone or as part of a larger moiety (e.g., as in "arylalkyleneoxy" or "arylhaloalkylenoxy"), refers to a saturated aliphatic hydrocarbon group with two radical points for forming two covalent bonds with two other moieties. It can contain 1 to 12 (e.g., 1 to 8, 1 to 6, or 1 to 4) carbon atoms. As a moiety, it can be denoted as $C_nH_{2n}$—. Examples of an alkylene group include, but are not limited to, methylene (—$CH_2$—), ethylene (—$CH_2CH_2$—), and propylene (—$CH_2CH_2CH_2$—). When an alkylene is preceded by a carbon-number modifier, e.g., $C_{2-8}$, its means the alkylene group contains 2 to 8 carbon atoms.

As used herein, the term "alkynyl," when used alone or as part of a larger moiety (e.g., as in "alkynylalkyl" or "haloalkynylalkoxy"), refers to an aliphatic hydrocarbon group with at least one triple bond. It can contain 2 to 12 (e.g., 2 to 8, 2 to 6, or 2 to 4) carbon atoms. An alkynyl group can be straight or branched. Examples of an alkynyl group include, but are not limited to, propargyl and butynyl. When an alkynyl is preceded by a carbon-number modifier, e.g., $C_{2-8}$, its means the alkynyl group contains 2 to 8 carbon atoms.

As used herein, the term "alkenyl," when used alone or as part of a larger moiety (e.g., as in "alkenylalkyl" or "alkenylalkoxy"), refers to an aliphatic hydrocarbon group with at least one double bond. It can contain 2 to 12 (e.g., 2 to 8, 2 to 6, or 2 to 4) carbon atoms. An alkenyl group with one double bond can be denoted as —$C_nH_{2n-1}$, or —$C_nH_{2n-3}$ with two double bonds. Like an alkyl group, an alkenyl group can be straight or branched. Examples of an alkenyl group include, but are not limited to, allyl, isoprenyl, 2-butenyl, and 2-hexenyl. When an alkylene is preceded by carbon-number modifier, e.g., $C_{3-8}$, its means the alkylene group contains 3 to 8 carbon atoms.

As used herein, the term "cycloalkyl," when used alone or as part of a larger moiety (e.g., as in "cycloalkylalkyl" or "halocycloalkylalkoxy"), refers to a saturated carbocyclic mono-, bi-, or tri-cyclic (fused or bridged or spiral) ring system. It can contain 3 to 12 (e.g., 3 to 10, or 5 to 10) carbon atoms. Examples of cycloalkyl groups include, but are not limited to, cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. When a cycloalkyl is preceded by a carbon-number modifier, e.g., $C_{3-8}$, its means the alkyl group contains 3 to 8 carbon atoms.

As used herein, the term "polyether" refers to a compound with more than one ether group. Examples of polyether includes those with alkyleneoxy [i.e., —RO—, in which R is an alkylene group, e.g., —CH$_2$O—, —CH$_2$CH$_2$O—, or CH$_2$CH(CH$_3$)O—] as the repeating unit.

As used herein, the term "cycloalkenyl," when used alone or as part of a larger moiety (e.g., as in "cycloalkenylalkyl" or "cyanocycloalkenylalkoxy"), refers to a non-aromatic carbocyclic ring system having one or more double bonds. It can contain 3 to 12 (e.g., 3 to 10, or 5 to 10) carbon atoms. Examples of cycloalkenyl groups include, but are not limited to, cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

As used herein, the term "heterocycloalkyl," when used alone or as part of a larger moiety (e.g., as in "heterocycloalkylalkyl" or "heterocycloalkoxy"), refers to a 3- to 16-membered mono-, bi-, or tri-cyclic (fused or bridged or spiral)) saturated ring structure, in which one or more of the ring atoms is a heteroatom (e.g., N, O, S, or combinations thereof). In addition to the heteroatom(s), the heterocycloalkyl can contain 3 to 15 carbon atoms (e.g., 3 to 12 or 5 to 10). Examples of a heterocycloalkyl group include, but are not limited to, piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A monocyclic heterocycloalkyl group can be fused with a phenyl moiety such as tetrahydroisoquinoline. When a heterocycloalkyl is preceded by a carbon-number modifier, e.g., C$_{4-8}$, its means the heterocycloalkyl group contains 4 to 8 carbon atoms.

As used herein, the term "hetero," when used alone or as part of a larger moiety (e.g., as in "heterocyclo" or "heterocycloalkyl" or "heteroaryl"), refers to a hetero atom or group that is —O—, —S—, —NH—, or —C(=O)—.

As used herein, the term "aryl," when used alone or as part of a larger moiety (e.g., as in "aralkyl", "aralkoxy," or "haloaryloxyalkyl"), refers to a monocyclic (e.g., phenyl), bicyclic (e.g., indenyl, naphthalenyl, or tetrahydronaphthyl), and tricyclic (e.g., fluorenyl, tetrahydrofluorenyl, tetrahydroanthracenyl, or anthracenyl) ring system in which the monocyclic ring system is aromatic (e.g., phenyl) or at least one of the rings in a bicyclic or tricyclic ring system is aromatic (e.g., phenyl). The bicyclic and tricyclic groups include, but are not limited to, benzo-fused 2- or 3-membered carbocyclic rings. For instance, a benzo-fused group includes phenyl fused with two or more C$_{4-8}$ carbocyclic moieties.

As used herein, the term "heteroaryl" refers to a monocyclic, bicyclic, or tricyclic ring system having 5 to 15 ring atoms wherein at least one of the ring atoms is a heteroatom (e.g., N, O, S, or combinations thereof) and when the monocyclic ring system is aromatic or at least one of the rings in the bicyclic or tricyclic ring systems is aromatic. It can contain 5 to 12 or 8 to 10 ring atoms. A heteroaryl group includes, but is not limited to, a benzo-fused ring system having 2 to 3 rings. For example, a benzo-fused group includes benzo fused with one or two 4- to 8-membered heterocycloalkyl moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, 1H-indazolyl, furyl, pyrrolyl, thienyl, thiazolyl, oxazolyl, imidazolyl, tetrazolyl, benzofuryl, isoquinolinyl, benzithiazolyl, xanthenyl, thioxanthenyl, phenothiazinyl, dihydroindolyl, benzo[1,3]dioxolyl, benzo[b]furyl, benzo[b]thiophenyl, indazolyl, benzimidazolyl, benzthiazolyl, puryl, quinolinyl, quinazolinyl, phthalazyl, quinazolyl, quinoxalyl, isoquinolinyl, 4H-quinolizyl, benzo-1,2,5-thiadiazolyl, and 1,8-naphthyridyl.

As used herein, the term "halo" refers to fluoro, chloro, bromo, or iodo.

As used herein, the term "alkylene-oxy-alkylene" refers to alkylene-O-alkylene, and example of which is —C$_2$H$_4$—O—C$_2$H$_4$—.

As used herein, the term "alkoxyalkyl" (or "alkyloxyalkyl") refers to alkyl-O-alkyl, and example of which is C$_2$H$_5$—O—C$_2$H$_4$—.

As used herein, the term "1,4-alkyl substituted piperazine" (or "1,4-dialkylpiperazine") refers to

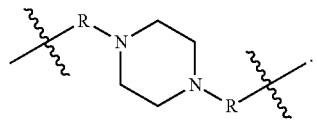

As used herein, the term "1,3-dioxan-5-amine" refers to

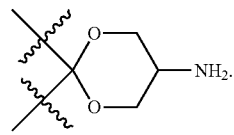 [SMILES: *C1(*)OCC(N)CO1]

As used herein, the term "1-alkylpiperazine" refers to

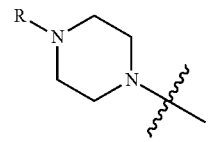

in which R is an alkyl group.

As used herein, the term "independent," e.g., as in "optionally substituted with one or more independent R$^3$ groups," means that when the number of substituent is more than one (e.g., two or three), these multiple substituents can be the same or different.

As used herein, the term "optionally" (e.g., as in "optionally substituted with") means that the moiety at issue is either substituted or not substituted, and that the substitution occurs only when chemically feasible. For instance, H cannot be substituted with a substituent and a covalent bond or —C(=O)— group cannot be substituted with a substituent.

As used herein, an "oxo" group refers to =O.

As used herein, a "carbonyl" group refers to —C(O)— or —C(=O)—.

As used herein, a "cyano" group refers to —CN.

As used herein, a "urea" group refers to the structure —NR$_X$—CO—NR$_Y$R$_Z$ when terminally included in a compound or —NR$_X$—CO—NR$_Y$— when internally included in a compound.

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

For convenience and as commonly understood, the term "optionally substituted" only applies to the chemical entities that can be substituted with suitable substituents, not to those that cannot be substituted chemically. Thus, it is effective only when chemically possible. For instance, when "$R^2$ is H, alkyl, aryl, heteroaryl, —C(═O)-alkyl, —C(═O)-aryl, or —C(═O)-heteroaryl, each of which is optionally substituted with one or more independent $Q^1$ groups." Although the phrase "each of which is optionally substituted with one or more independent $Q^1$ groups" grammatically applies to H, hydrogen atoms (H) cannot be chemically substituted, therefore the phase does not actually apply to H. As another example, when "L' is a covalent bond, —C(═O)—, —C(═O)-alkylene, or alkylene, each of which is optionally substituted with one or more independent $R^4$ groups," the phrase "each of which is optionally substituted with one or more independent $R^4$ groups" will not apply to a covalent bond or —C(═O)— since these two are not possible to be chemically substituted.

As used herein, the term "derivative" (or "analogue') refers a compound that is derived from a compound that is not similar in chemical or physical process. For instance, if one atom in an initial compound is replaced with another atom or group of atoms, the resultant compound is considered as a derivative or analog of the initial compound.

As used herein, the term "or" can mean "or" or "and."

DETAILED DESCRIPTION OF THE INVENTION

The present invention provides compounds of Formula I:

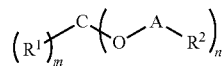

wherein m is 2, 1, or 0; n is 2, 3, or 4; the sum of m and n is 4; each $R^1$ is independently hydrogen, alkyl, cycloalkyl, heterocycle, heterocycloalkyl, alkenyl, cycloalkenyl, aryl, heteroaryl, alkoxyalkyl, or alkynyl; each A is independently alkyl, alkylene, alkenene, alkylene-hetero-alkylene, alkylene-heterocyclo-alkylene, carbonyl, thiocarbonyl, alkylene-oxy-alkylene, 1,4-alkyl substituted piperazine, aryl, or heteroaryl. Each $R^2$ is independently —$NHR^3$, heterocycloalkyl, or —SH, wherein each $R^3$ is independently hydrogen, alkyl, cylcoalkyl, heterocycle, alkenyl, aryl, or heteroaryl. Alternatively, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group.

These compounds include di-, tri-, or polyvalent cleavable links between the core and the nucleophilic end groups. As such, they can be used as hardeners or cross-linkers for curing thermosetting polymers such as epoxies (due to the terminal nucleophilic groups), but can also enable the breakdown or degradation of the cured resins (due to the cleavable bonds). These compounds can include the functionality of formal, ketal, acetal, orthoester, or orthocarbonate and they tend to be acid labile. See below the general structural schemes of such compounds.

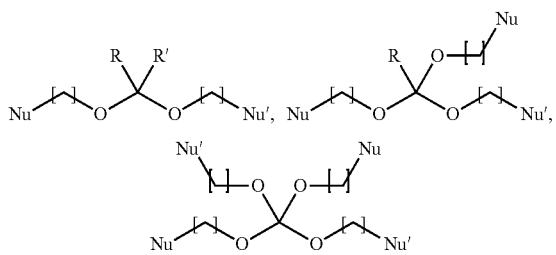

Although synthesis of tertiary aminoorthoesters has been described in the art (see, e.g., U.S. Pat. No. 3,786,029), the synthesis of aminoorthoesters that contain primary- or secondary-amines has not been previously reported. As such, another aspect of this invention provides methods for making the compounds of Formula I (e.g., aminoorthoseters that contain primary- or secondary amines, thiolorthoseters, and thiolorthocarbonates).

The present invention also encompasses the use of the compounds of Formula I as amino- or thiol hardeners for curing epoxy resins to give degradable cross-linked resins. U.S. Pat. No. 5,932,682 disclosed the use of ketal containing diepoxides cured with anhydrides, for reworkable epoxy systems. However, the curing of ketal, orthoester or orthocarboante-based epoxy resins with amine- or thiol-based hardeners and their mild acid degradation has hitherto not been disclosed. As such, another aspect of this invention is that it provides a method for curing ketal, acetal, orthoester, or orthocarbonate resins of the general types shown below, with amine- or thiol-based hardeners of this invention used for the production of reworkable epoxy compositions. Resins cured in such a way are also within the scope of this invention.

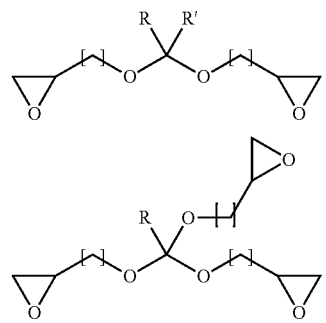

23

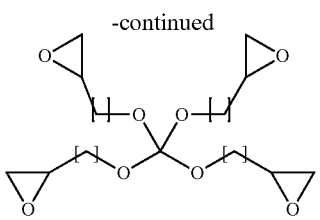
-continued

The use of orthoester and orthocarbonate linkage is also suitable for thiol-based hardeners. Thiol hardeners serve as the basis for fast curing systems, commonly with set times of less than 15 minutes.

The present invention includes, as non-limiting examples, fully acid recyclable hardeners, acid recyclable hardener-resin compositions, ultra-fast setting thiol-based reworkable epoxies, reworkable epoxies, wash-away epoxies, reworkable ultra clear epoxies, reworkable epoxy pastes, and reworkable epoxy putties, and other such compositions. Such compositions can be degraded in acidic conditions, especially weakly acidic conditions. The present invention further includes, as non-limiting examples, recyclable hardener-resin compositions that are resistant to degradation under weekly acidic conditions, and can only be readily dissolved or reworked under more strongly acidic conditions. The advantages of the present invention include, without limitation, the ability to form easily acid-degradable epoxy compositions using compounds of Formula I where the ability to remove, reverse or otherwise recycle the epoxy composition or the component(s) in contact with the epoxy compositions is desired. For example, a composition provided by the present invention can be used to seat an electronic component in an epoxy coating and then that component can be recovered, removed or recycled at a later time by removing the epoxy composition under conditions that do not damage the component or mother structure. As another example, a composition provided by the present invention that can only be dissolved under more strongly acidic conditions can be used to manufacture carbon fiber composites, which at a later time the carbon fiber can be recovered by removing the epoxy matrix under conditions that do not significantly adversely affect the properties of the carbon fiber. As another example, a composition provided by the present invention that can only be dissolved under more strongly acidic conditions can be used in commercial or residential construction applications such as in epoxy flooring or epoxy countertops, which at a later time can be recycled. As another example, the thiol orthoesters of this invention could be used with an existing epoxy resin to produce a fast curing epoxy system whose excess could be easily wiped away by, e.g., an unskilled user needing to bond two components together in their home, office, place of work, automobile, nautical craft, etc. A further advantage of the present invention is the ability to recycle devices that contain high-value material components that can be reused or reutilized. For example, indium or indium-tin-oxide can be recovered from thin-films held together in devices typically employing epoxy adhesives, such as cellular telephones, portable television screens, and the like.

The compounds of Formula I can be used as hardeners in epoxy compositions to achieve cured compositions that can be degraded in acidic conditions, ranging from weakly to strongly acidic conditions. Such a strategy is attractive because it allows common resins to be combined with novel hardeners for the formation of epoxies with a variety of mechanical, adhesive, electronic, thermal etc. properties, while enabling them to be disassembled, dissolved, or reworked. The development of epoxy systems employing acid-labile hardeners where the cured resin can rapidly disassemble under mildly acidic conditions while maintaining mechanical and adhesive integrity in the ambient environment, as described in this invention, are unknown in the prior art. As such, the present invention also provides: (1) the use of orthoesters to produce hardener components of epoxy compositions that enable useful degradation properties including degradation under mildly acidic conditions; (2) the use of formal, ketal, acetal moieties, suitable derivatives, and analogs as hardener component in epoxy compositions; (3) the use of orthocarbonate moieties, suitable derivatives, and analogs as hardener component in epoxy compositions, (4) the use of ketal, acetal, orthoester, or orthocarbonate based epoxy resins with non degradable polyamine or polythiol hardener components to provide compositions that enable useful degradation properties including degradation under mildly acidic conditions.

Set forth below are examples of the compounds of this invention and methods of making and using them. They are intended to be illustrative and not to be constructed as limiting the scope of this invention in any way.

Example 1

Synthesis of Amino Ketal

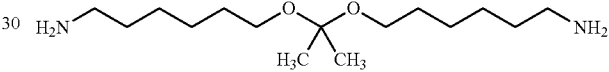

N-(6-hydroxyhexyl)pthalimide (50 g, 202 mmol), 2,2-dimethoxypropane (21 g, 202 mmol), and a catalytic amount of p-toluene sulfonic acid monohydrate (192.3 mg, 1 mmol, 0.005 equiv.) were placed in 200 mL of toluene in a 500 mL Round Bottom Flask equipped with a 25 mL Dean Stark apparatus. The reaction was heated to reflux and the Dean Stark column emptied every 5 hours. After 20 hours, the reaction mixture was cooled to ambient temperature and concentrated under reduced pressure. The resulting crude residue was dissolved in 50 mL of THF and then 80% hydrazine hydrate (80 g, 1280 mmol) was added and the reaction mixture was heated to reflux again. After 10 hours, the reaction was cooled to room temperature, filtered and concentrated under reduced pressure. The resulting crude oil was dissolved in dichloromethane, the solution washed with water and brine, dried with $Na_2SO_4$, and then concentrated under reduced pressure to give 20 g of the title compound (72% yield).

$^1$H NMR ($CDCl_3$, 400 MHz): 3.39 (t, J=6.8 Hz, 4H), 2.68 (t, J=6.8 Hz, 4H), 1.56-1.51 (m, 4H), 1.47-1.42 (m, 4H), 1.34 (bs, 14H), 1.20 (bs, 4H). $^{13}$C NMR ($CDCl_3$, 100 MHz):99.5, 60.6, 42.2, 33.8, 30.1, 26.8, 26.3, 25.0.

Example 2

Synthesis of Amino Orthoesters

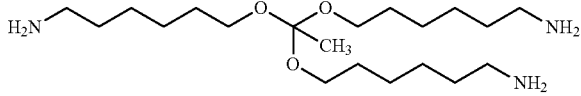 [SMILES: CC(OCCCCCCN)(OCCCCCCN)OCCCCCCN]

N-(6-hydroxyhexyl)pthalimide (140 g, 567 mmol), triethyl orthoacetate (31 g, 195 mmol), and a catalytic amount of p-toluene sulfonic acid monohydrate (31.9 mg, 0.168 mmol, 0.0009 equiv.) were placed in 700 mL of cyclohexane. The reaction mix was heated to reflux and the evolved ethanol removed via distillation of the cyclohexane/ethanol azeotrope (vapor temperature 60-80.5° C.). After the reaction vapor temperature reached 80.5° C., the reaction mixture was heated for additional 30 minutes. Subsequently, the solution was cooled to ambient temperature and the solvent removed under reduced pressure. The resulting crude residue was dissolved in 800 mL of THF and then 80% hydrazine hydrate (222.3 g, 3.8 mol) was added and the reaction heated to reflux. After 10 hours, the reaction was cooled to room temperature, filtered, and concentrated under reduced pressure. The resulting crude oil was dissolved in dichloromethane, the solution washed with water and brine, dried with $Na_2SO_4$, and then concentrated under reduced pressure to give 36 g of the title compound (49% yield).

$^1$H NMR (CDCl$_3$, 400 MHz): 3.45 (t, J=6.8 Hz, 6H), 2.68 (t, J=6.8 Hz, 6H), 1.60-1.54 (m, 6H), 1.49-1.29 (m, 27H); $^{13}$C NMR (CDCl$_3$, 100 MHz): 114.0, 61.8, 42.0, 33.6, 29.6, 26.7, 26.1, 20.1.

Example 3

Synthesis of Amino Orthocarbonates

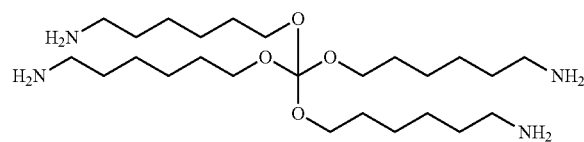 [SMILES: NCCCCCCOC(OCCCCCCN)(OCCCCCCN)OCCCCCCN]

N-(6-hydroxyhexyl)pthalimide (20 g, 80.8 mmol), tetraethyl orthocarbonate (4.13 g, 20 mmol), and a catalytic amount of p-toluene sulfonic acid monohydrate (3.4 mg, 0.0179 mmol, 0.0009 equiv.) were placed in 100 mL of cyclohexane. The reaction mix was heated to reflux and the evolved ethanol removed via distillation of the cyclohexane/ethanol azeotrope (vapor temperature 60° C.). After the reaction vapor temperature reached 80.5 C, the reaction was heated for an additional 30 min. Subsequently, the solution was cooled to ambient temperature and the solvent removed under reduced pressure. The resulting crude residue was dissolved in 50 mL of THF and then 80% hydrazine hydrate (36 g, 576 mmol) was added and the reaction heated to reflux. After 10 hours, the reaction was cooled to room temperature, filtered, and concentrated under reduced pressure. The resulting crude oil was dissolved in dichloromethane, the solution washed with water and brine, dried with $Na_2SO_4$, and then concentrated under reduced pressure to give 4.5 g of the title compound (47% yield).

$^1$H NMR (CDCl$_3$, 400 MHz): 3.49 (t, J=6.8 Hz, 8H), 2.68 (t, J=6.8 Hz, 8H), 1.63-1.56 (m, 8H), 1.48-1.32 (m, 24H), 1.17 (s, 8H).

$^{13}$C NMR (CDCl$_3$, 100 MHz): 119.5, 62.6, 42.1, 33.7, 29.2, 26.7, 26.1.

Example 4

Synthesis of Thiol Orthoseters

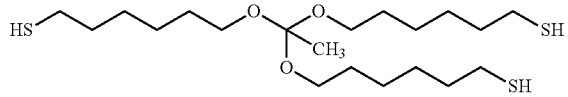 [SMILES: CC(OCCCCCCS)(OCCCCCCS)OCCCCCCS]

6-Chlorohexan-1-ol (100 g, 735 mmol), triethyl orthoacetate (36 g, 204 mmol), and a catalytic amount of p-toluene sulfonic acid (38 mg, 0.221 mmol) were placed in 700 mL of cyclohexane. The reaction mix was heated to reflux and the evolved ethanol removed via distillation of the cyclohexane/ethanol azeotrope (vapor temperature 60-80.5° C.). After the reaction vapor temperature reached 80.5° C., the reaction mixture was heated for additional 60 minutes. Subsequently, the solution was cooled to ambient temperature and the solvent removed under reduced pressure. The resulting crude residue was dissolved in 1000 mL of DMF and then $K_2CO_3$ (191.6 g, 1.39 mol) was added. After stirring for 20 hours, the reaction solution was filtered, concentrated under reduced pressure, then water was added, extracted with DCM, washed with brine, dried over anhydrous $Na_2SO_4$, and then concentrated under reduced pressure. The resulting crude residue was dissolved in 144 mL of THF and 50% hydrazine hydrate (72 g, 0.72 mol) was added and the reaction was heated to 35° C. After 12 hours, the reaction was cooled to room temperature and concentrated under reduced pressure. The resulting crude oil was dissolved in dichloromethane, the solution washed with water and brine, dried with $Na_2SO_4$, and then concentrated under reduced pressure to give 32 g of the title compound (41.8% yield).

$^1$H NMR (CDCl$_3$, 400 MHz): 1.34 (t, J=7.6 Hz), 1.36-1.43 (m), 1.43 (s), 2.52 (q, J$_{av}$=7.4 Hz), 3.43 (t, J$_{av}$6.6 Hz).

Example 5

Synthesis of Thiol Orthocarbonates

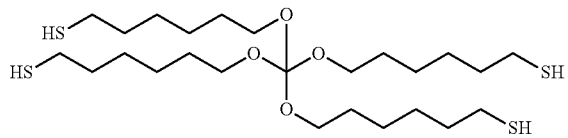 [SMILES: SCCCCCCOC(OCCCCCCS)(OCCCCCCS)OCCCCCCS]

The mixture of S-6-hydroxyhexyl ethanethioate (20 g, 114 mmol), tetraethyl orthocarbonate (4.2 g, 21.9 mmol), and a catalytic amount of p-toluene sulfonic acid (8 mg, 0.047 mmol) was heated to 150° C. and the evolved ethanol removed via distillation (vapor temperature 35-78° C.). After the reaction, vapor temperature reached 78° C. and the reaction mixture was heated for additional 60 minutes. Subsequently, the solution was cooled to ambient temperature, $K_2CO_3$ (2 g, 14.5 mmol) was added and the solvent removed under reduced pressure. The resulting crude residue was dissolved in 300 mL of THF and 80% hydrazine hydrate (19 g, 0.304 mol) was added and the reaction was heated to 50° C. After 3 hours, the reaction was cooled to room temperature and concentrated under reduced pressure. The resulting crude oil was dissolved in dichloromethane, and the solution was washed with water and brine, dried with Na$_2$SO$_4$, and then concentrated under reduced pressure to give 6.5 g of the title compound (54.6% yield). $^1$H NMR (CDCl$_3$, 400 MHz): 1.34 (t, J$_{av}$=7.8 Hz), 1.37-1.42 (m), 1.56-1.65 (m), 2.52 (q, J$_{av}$=7.4), 3.49 (t, J=6.8 Hz).

Example 6

Curing of Bisphenol A Dyglycidyl Ether with Amine Hardeners

Bisphenol A dyglycidyl ether [BPADGE] is a standard resin used in the epoxy industry. BPADGE (epoxide equivalent weight=180-182) was mixed with the different cleavamine hardeners and then dispensed in 5×3 mm circular aluminum pan. The samples were cured at 100° C. in the oven, and then the resin was removed from the pan.

Example 6a

The same procedure as described immediately above was carried out with 100 parts BPADGA and 38 parts amino ketal from example 1 to give a hard tack-free solid.

Example 6B

The same procedure as described immediately above was carried out with 100 parts BPADGA and 35 parts amino orthoester from example 2 to give a hard tack-free solid.

Example 6C

The same procedure as described immediately above was carried out with 100 parts BPADGA and 33 parts amino orthocarbonante from example 3 to give a hard tack-free solid.

Example 7

Curing of Bisphenol A Dyglycidyl Ether with Amine Thiol Hardeners

Different thiol hardeners were mixed with BPADGE (epoxide equivalent weight=185-192) and 2,4,6-tri(dimethylaminomethyl)phenol [TDMAP] was used as the accelerator. The samples were cured at ambient temperature in a plastic dish. Gelling of the formulation was apparent in less than one hour.

Example 7a

The same procedure as described immediately above was carried out with 100 parts BPADGA, 75 parts thiol otrthoester from example 4 and 8 parts TDMAP to give a hard, tack-free solid.

Example 7B

The same procedure as described immediately above was carried out with 100 parts BPADGA and 72 parts thiol orthocarbonate from example 5 and 8 parts TDMAP to give a hard, tack-free solid.

Example 8

Disassembly of BPADGE/CLEAVAMINE Resins

The cured epoxy resins were placed in a solution of water/ethanol/acetic acid (50/45/5 percent respectively), but could also be placed in water/ethanol (50/50 percent respectively), at 50° C. After 12 h, the resins were examined. Samples 6A, 6B, and 6C had all completely dissolved in the 12-hour period in the acid solution, with 6D only remaining in small gel-like pieces. In drastic contrast, all of the resins remained as hard, tack free resins after the prolonged immersion in the non-acid solution, with no weight loss detected after immersion.

Example 9

An example of the novel characteristics of this degradable epoxy was demonstrated. A porcelain teacup that had broken in two pieces was glued back together using a cleavamine-HT/BPADGE formulation. After curing, noticeable amounts of hard cured resin existed on surface surrounding the joint closure. After immersion of the teacup in a solution of 10% acetic in ethanol/water (1:1 mixture), the spilled-over resin dissolved or could be wiped from the surface, with the bonding of the joint remaining steadfast. The newly bonded joint could not be pulled apart by hand.

Example 10

An example of the novel characteristics of this degradable epoxy was demonstrated. A quartz glass tube that had broken in two pieces was glued back together using a mercaptocleave-HQ/BPADGE formulation (as in example 7b). After curing, the hardened epoxy that spilled from the pressed joint was easily removed after the quartz tube had been immersed in a 1:1 mixture of ethanol and white vinegar for two hours. Any epoxy that did not dissolve was easily wiped from the quatz with a paper towel. The bonded joint remained intact after the immersion.

Other Embodiments

The invention has been described above with the reference to specific examples and embodiments. It is understood that various modifications and additions can be made to the specific examples and embodiments disclosed without departing from the spirit of the invention, and all such modifications and additions are contemplated as being part of the present invention.

What is claimed is:
1. An epoxy resin composition comprising:
an epoxy resin; and
a polyamine curing agent comprising a compound having Formula (I):

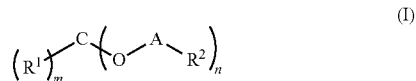

wherein:
m is 2, 1, or 0;
n is 2, 3, or 4;
the sum of m and n is 4;
each R$^1$ is independently hydrogen, alkyl, cycloalkyl, heterocycle, heterocycloalkyl, alkenyl, cycloalkenyl, aryl, heteroaryl, alkyloxyalkyl, or alkynyl;
each A is independently unsubstituted ethylene, propylene, isopropylene, butylene, iso-butylene, hexylene, ethylene-oxy-ethylene, ethylene-amino-ethylene,

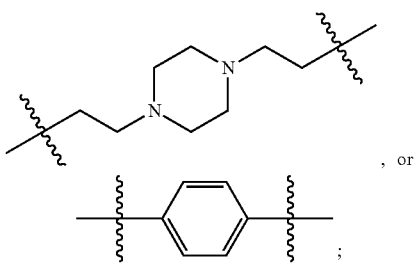
, or each $R^2$ is independently —$NHR^3$, wherein each $R^3$ is independently hydrogen, alkyl, aminoalkyl, alkylaminoalkyl, cycloalkyl, heterocycle, alkenyl, aryl, or heteroaryl;

or, every two —O-A-$R^2$ groups, together with the carbon atom to which they are attached to, can independently form an dioxanyl ring with no less than 4 ring members and one or more of the ring carbon atom(s), other than the carbon atom to which the two —O-A-$R^2$ groups are attached, are independently substituted with one or more independent amino group or aminoalkyl wherein each amino is independently a primary or secondary amino group.

2. An adhesive material comprising the epoxy resin composition of claim 1.

3. A coating material comprising the epoxy resin composition of claim 1.

4. A composite matrix material comprising the epoxy resin composition of claim 1.

5. The composition of claim 1, wherein $R^1$ is independently hydrogen, alkyl, or aryl.

6. The composition of claim 1, wherein $R^1$ is independently hydrogen or methyl.

7. The composition of claim 1, wherein the compound is:

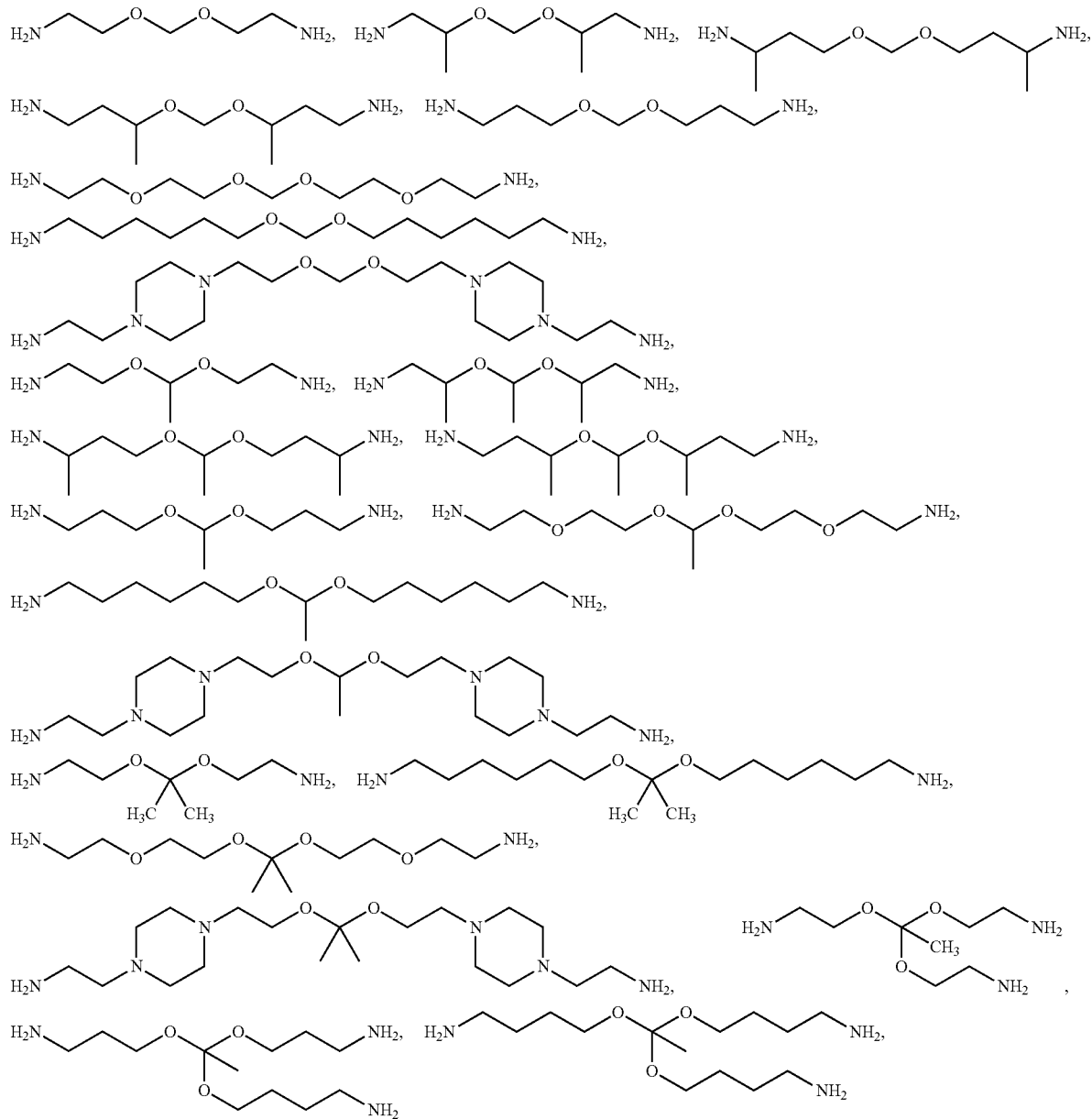

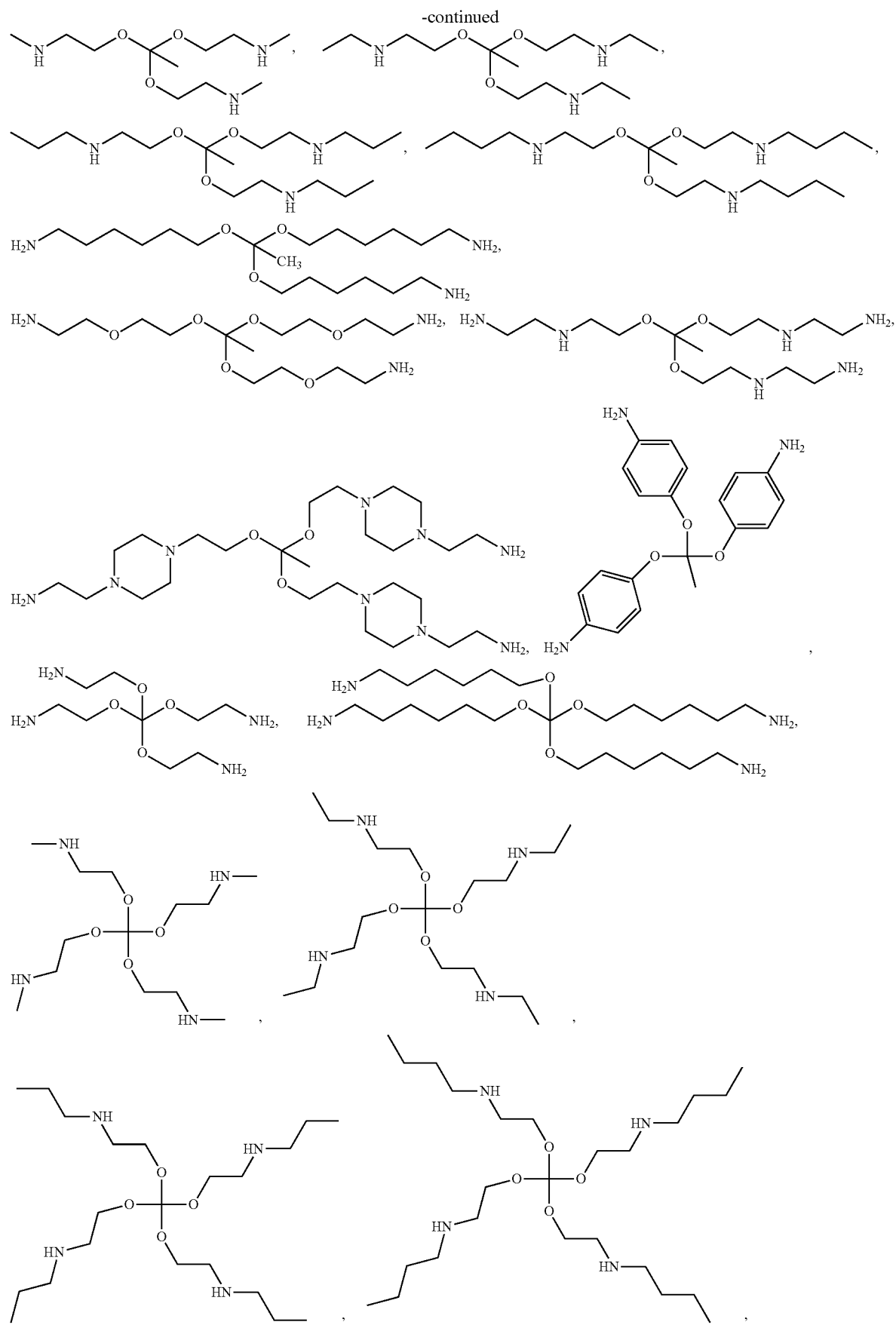

-continued
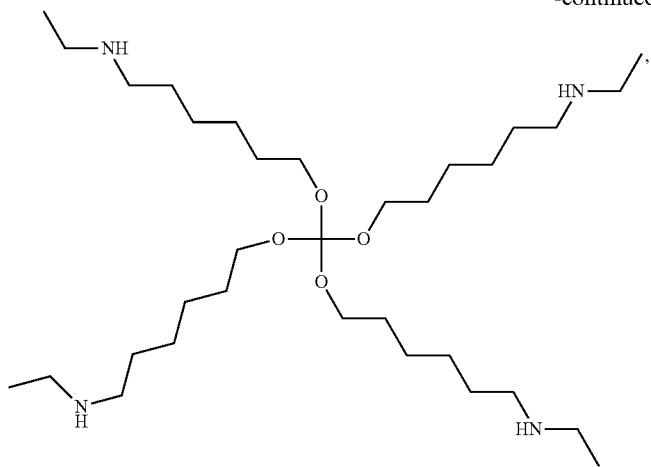
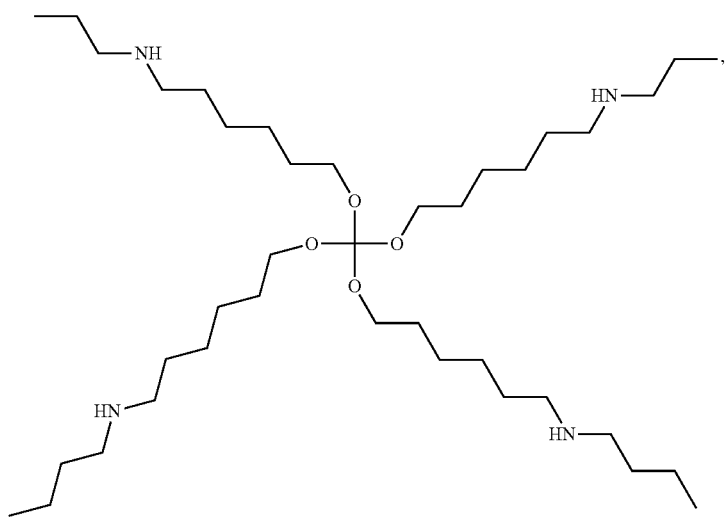
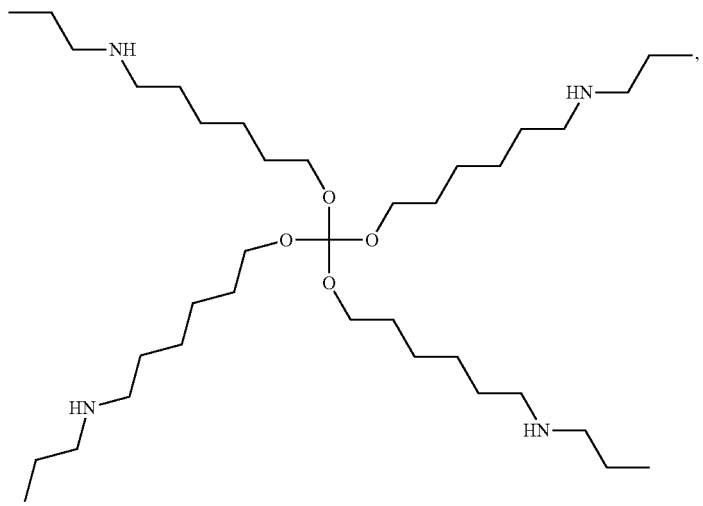

-continued
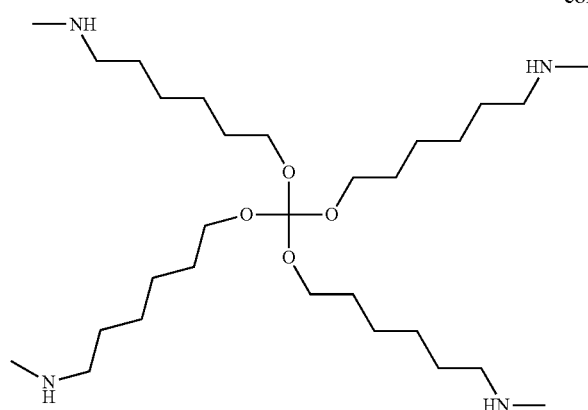 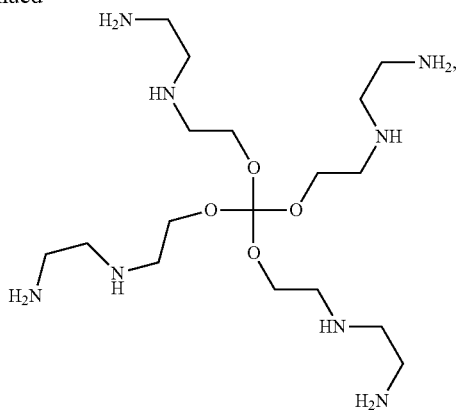
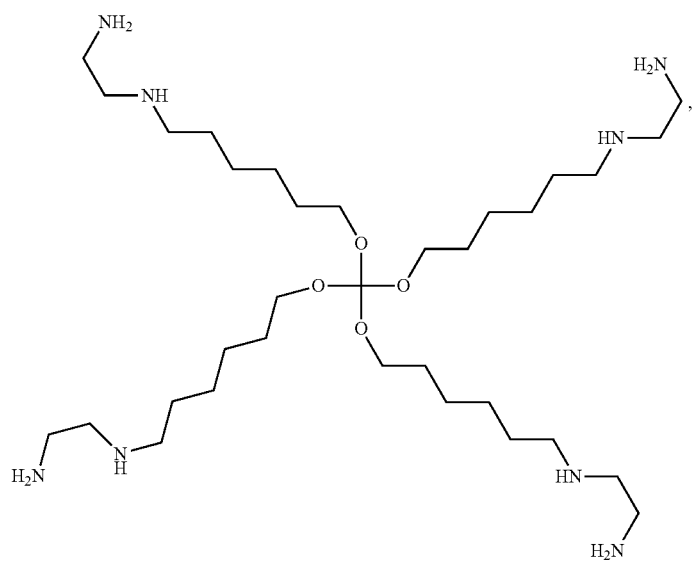
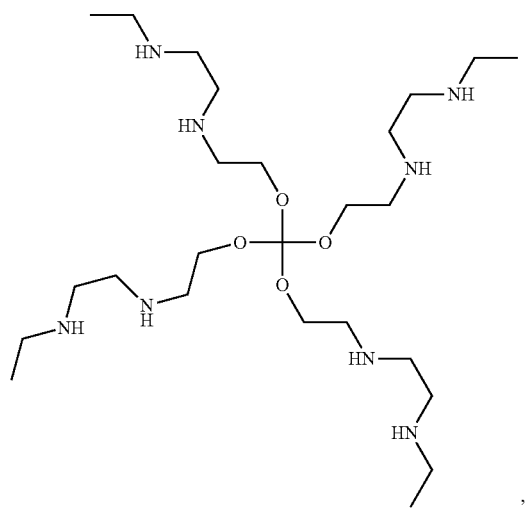

-continued

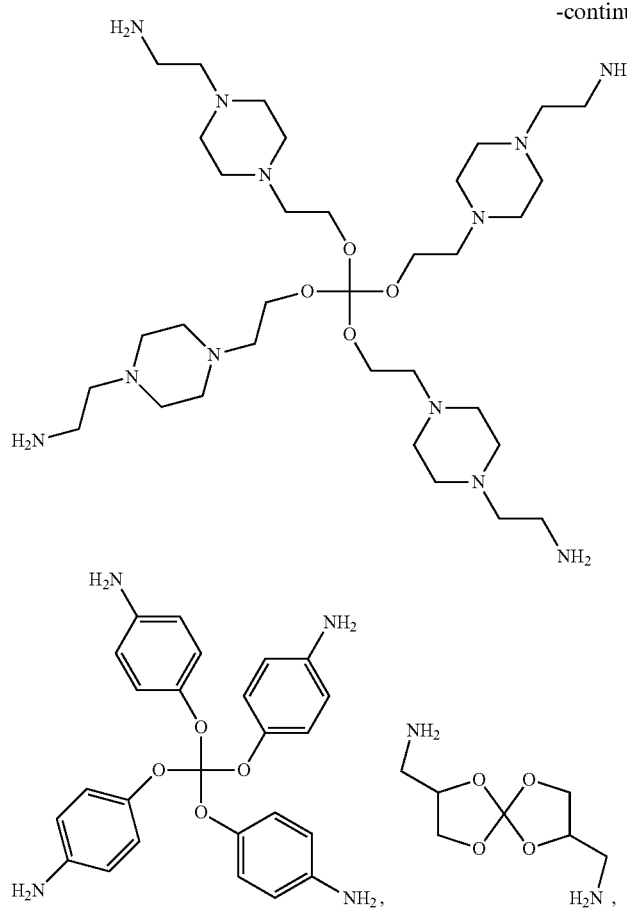

8. The composition of claim 1, wherein the compound is:

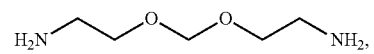
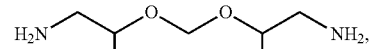
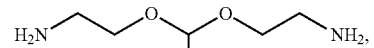
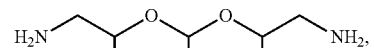
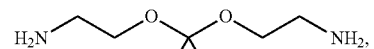
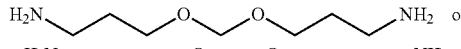
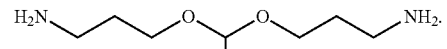

9. A composite comprising a cross-linked epoxy resin in contact with a substrate, wherein the cross-linked polymer comprises cleavable links derived from a cross-linking agent comprising a compound having Formula (I):

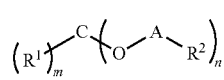

wherein:
  m is 2, 1, or 0;
  n is 2, 3, or 4;
  the sum of m and n is 4;
  each $R^1$ is independently hydrogen, alkyl, cycloalkyl, heterocycle, heterocycloalkyl, alkenyl, cycloalkenyl, aryl, heteroaryl, alkyloxyalkyl, or alkynyl;
  each A is independently unsubstituted ethylene, propylene, isopropylene, butylene, iso-butylene, hexylene, ethylene-oxy-ethylene, ethylene-amino-ethylene,

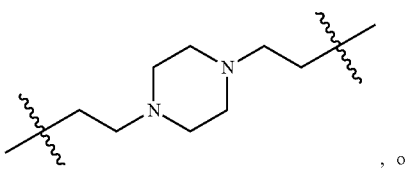
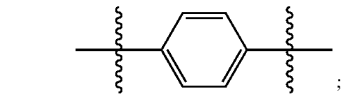

each R² is independently —NHR³, wherein each R³ is independently hydrogen, alkyl, aminoalkyl, alkylaminoalkyl, cycloalkyl, heterocycle, alkenyl, aryl, or heteroaryl;

or, every two —O-A-R² groups, together with the carbon atom to which they are attached to, can independently form an dioxanyl ring with no less than 4 ring members and one or more of the ring carbon atom(s), other than the carbon atom to which the two —O-A-R² groups are attached, are independently substituted with one or more independent amino group or aminoalkyl wherein each amino is independently a primary or secondary amino group.

10. The composite of claim 9, wherein R¹ is independently hydrogen, alkyl, or aryl.

11. The composite of claim 9, wherein R¹ is independently hydrogen or methyl.

12. The composite of claim 9, wherein the compound is:

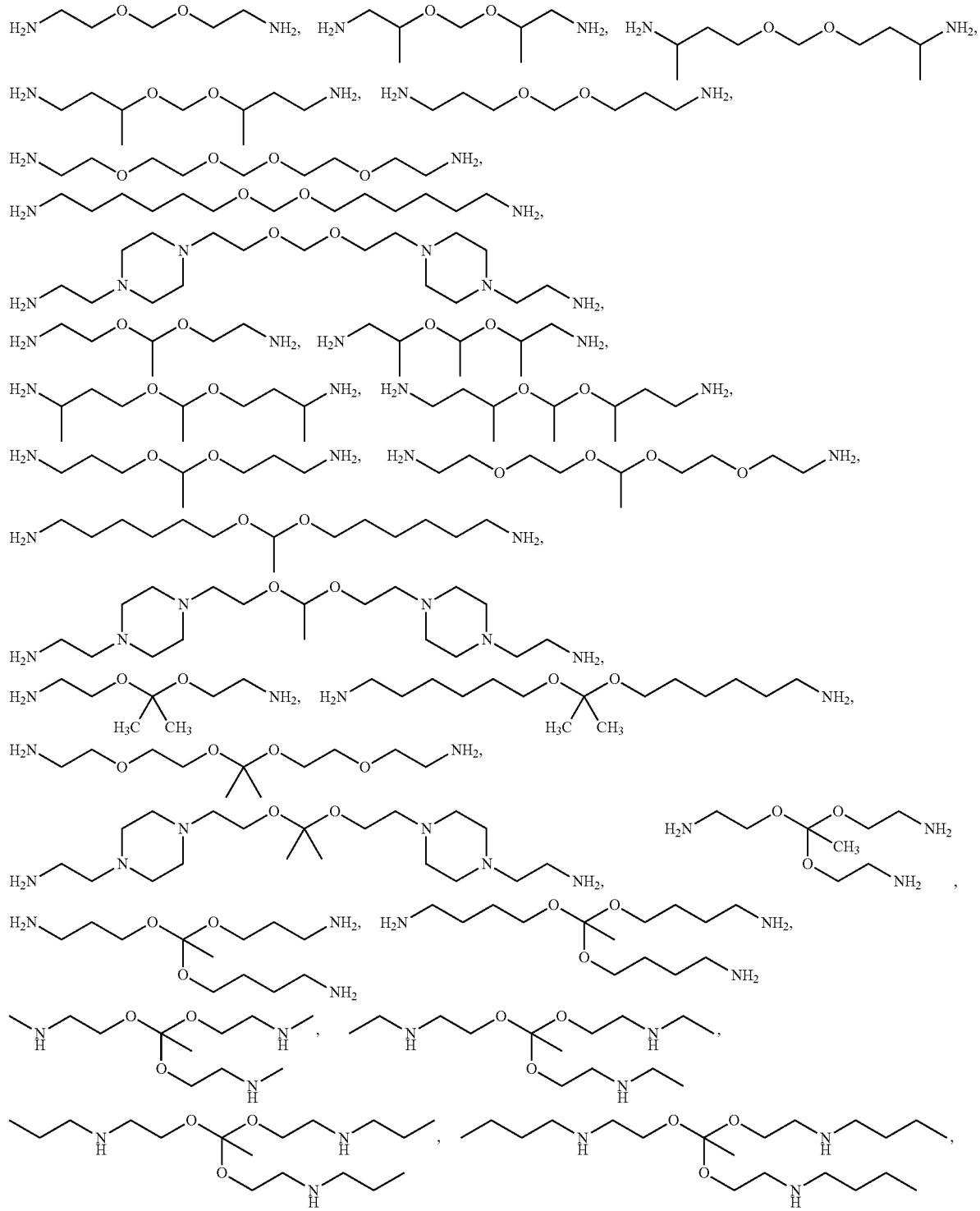

-continued
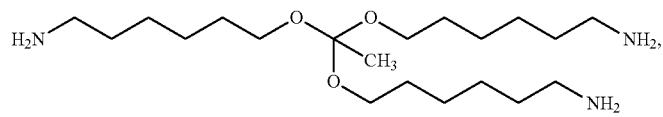
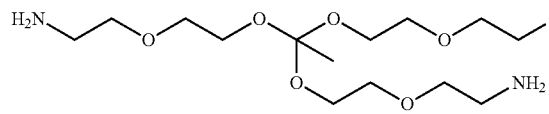
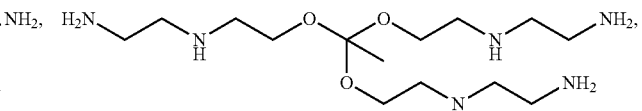
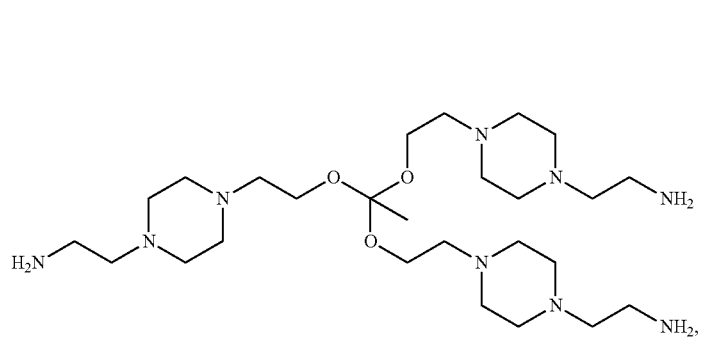
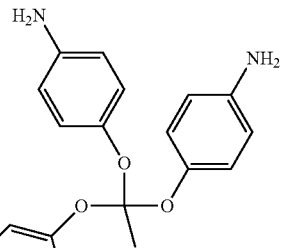
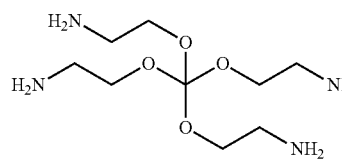
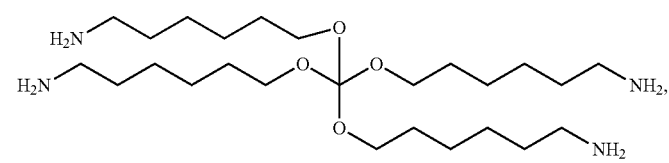
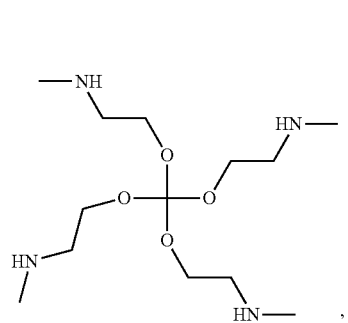
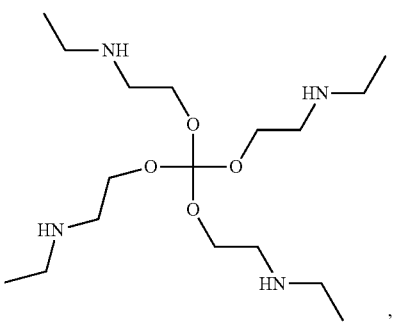
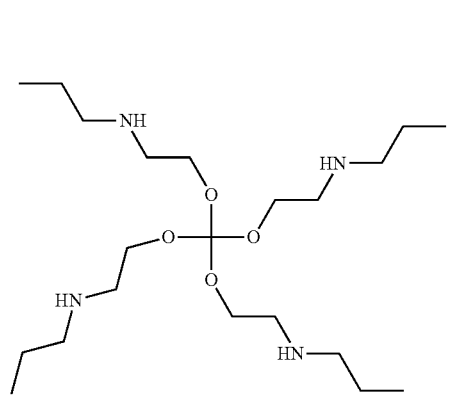
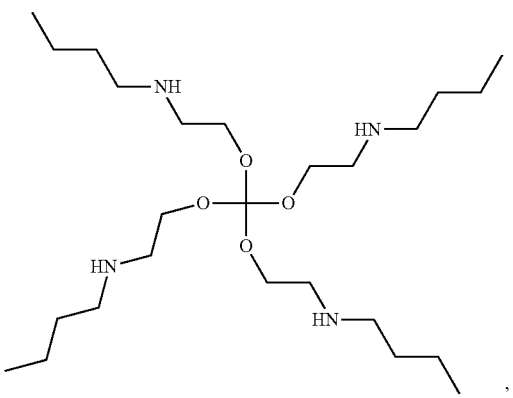

-continued
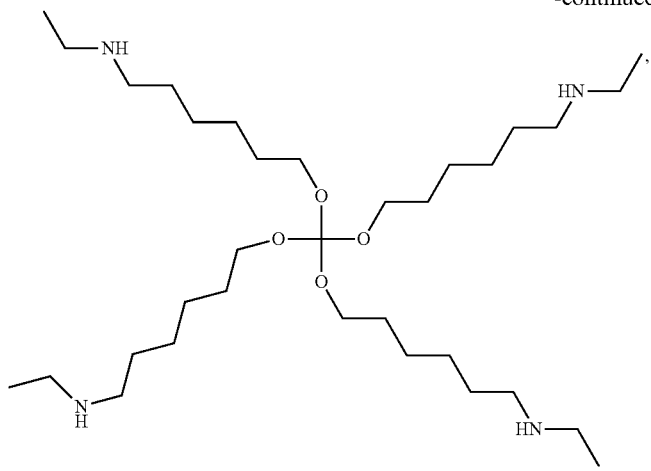
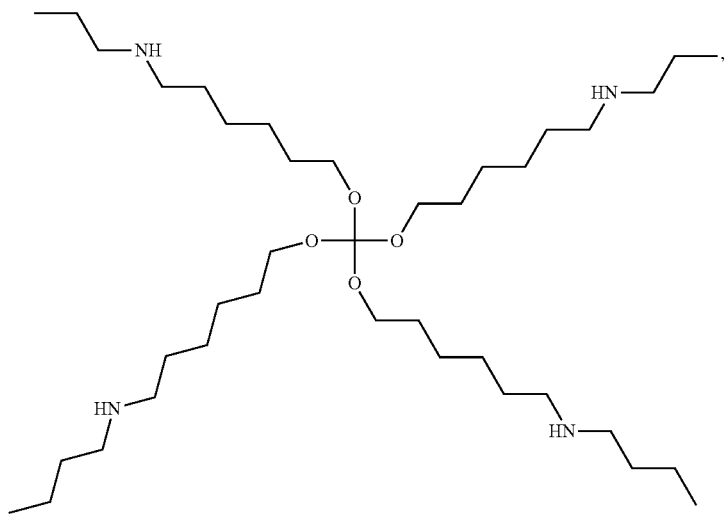
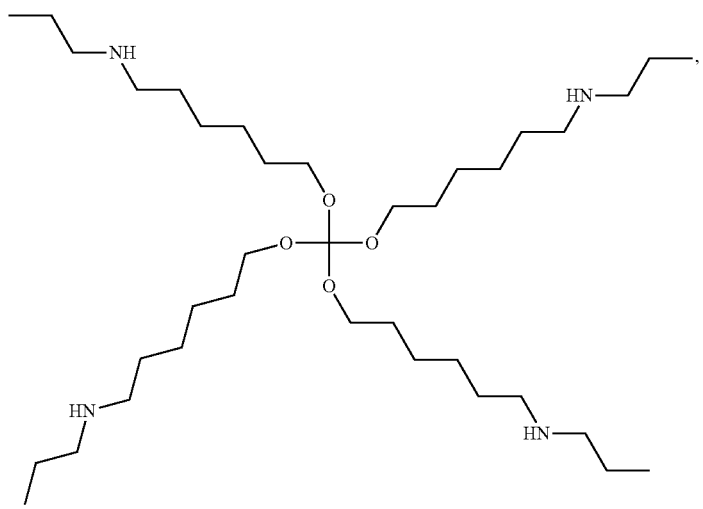

-continued
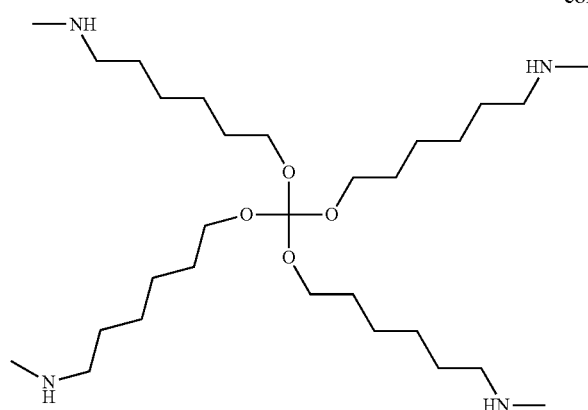
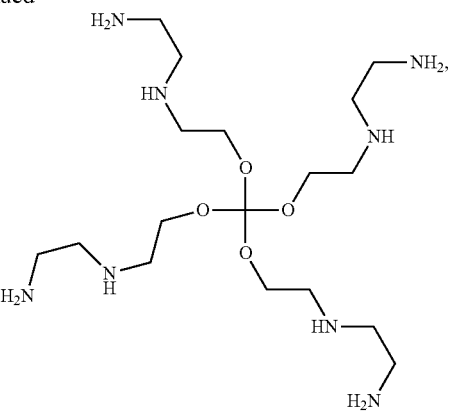
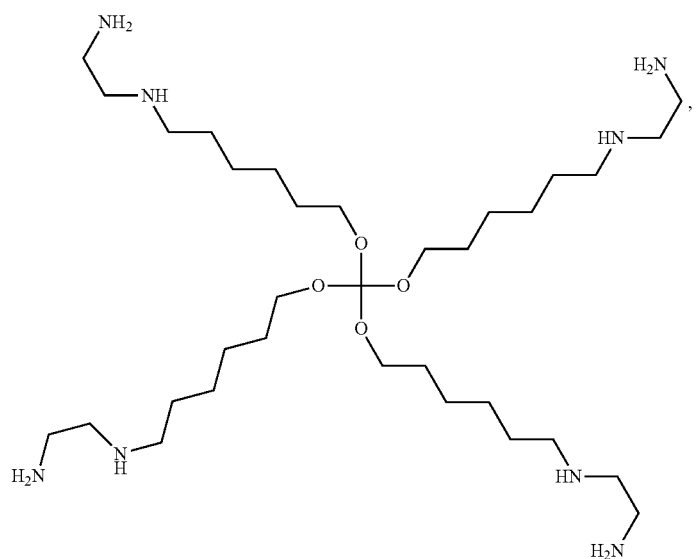
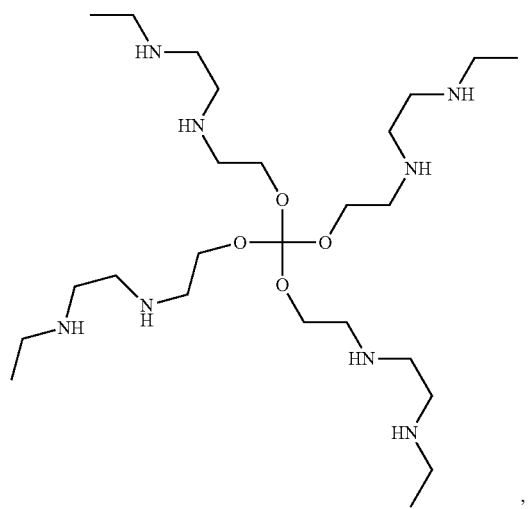

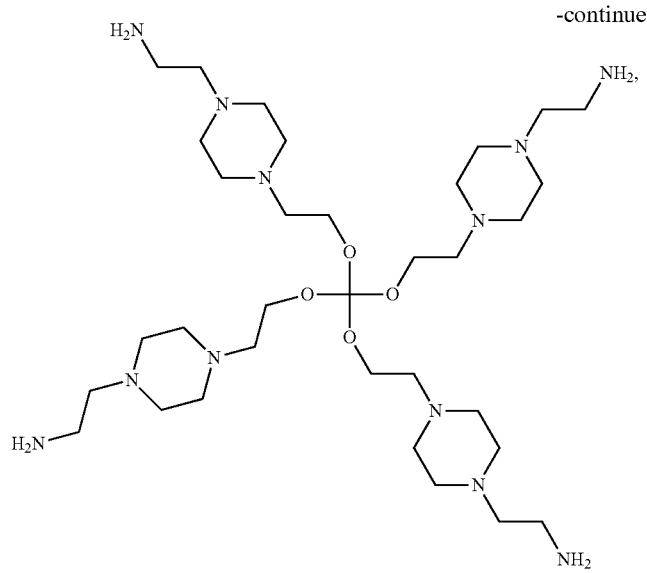

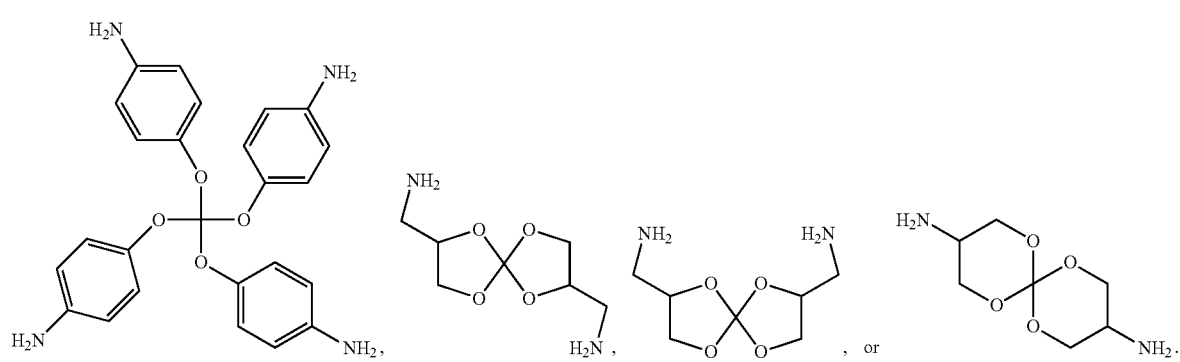

13. The composite of claim 9, wherein the compound is:

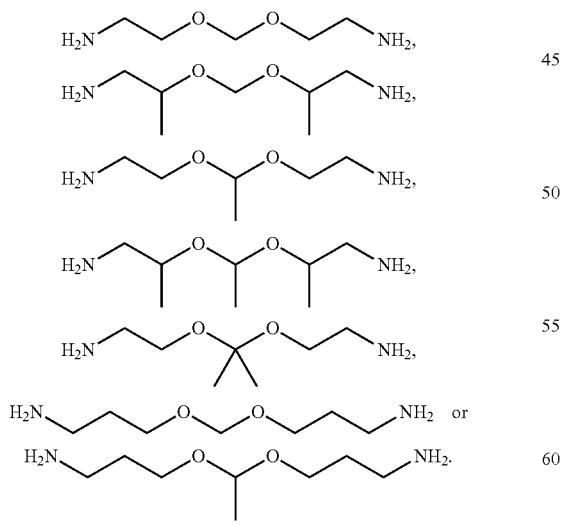

14. A cross-linked epoxy matrix derived from an epoxy resin and cross-linking group derived from a polyamine curing agent having the structure of Formula (I):

$$\left(R^1\right)_m C \left(O - A - R^2\right)_n \quad (I)$$

wherein:
m is 2, 1, or 0;
n is 2, 3, or 4;
the sum of m and n is 4;
each $R^1$ is independently hydrogen, alkyl, cycloalkyl, heterocycle, heterocycloalkyl, alkenyl, cycloalkenyl, aryl, heteroaryl, alkyloxyalkyl, or alkynyl;
each A is independently unsubstituted ethylene, propylene, isopropylene, butylene, iso-butylene, hexylene, ethylene-oxy-ethylene, ethylene-amino-ethylene,

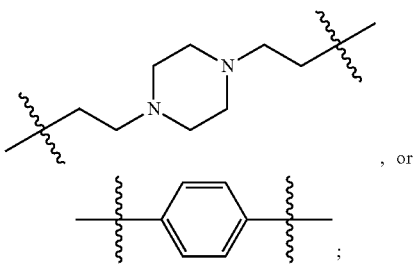

each R² is independently —NHR³, wherein each R³ is independently hydrogen, alkyl, aminoalkyl, alkylaminoalkyl, cycloalkyl, heterocycle, alkenyl, aryl, or heteroaryl;

or, every two —O-A-R² groups, together with the carbon atom to which they are attached to, can independently form an dioxanyl ring with no less than 4 ring members and one or more of the ring carbon atom(s), other than the carbon atom to which the two —O-A-R² groups are attached, are independently substituted with one or more independent amino group or aminoalkyl wherein each amino is independently a primary or secondary amino group.

15. The epoxy matrix of claim 14, wherein R¹ is independently hydrogen, alkyl, or aryl.

16. The epoxy matrix of claim 14, wherein R¹ is independently hydrogen or methyl.

17. The epoxy matrix of claim 14, wherein the compound is:

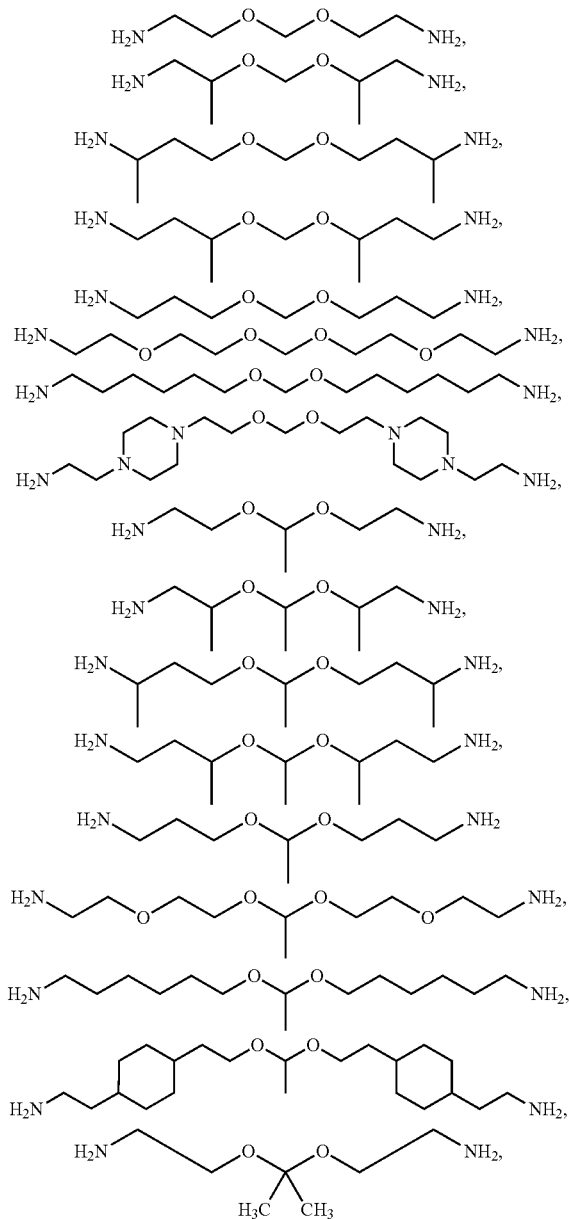
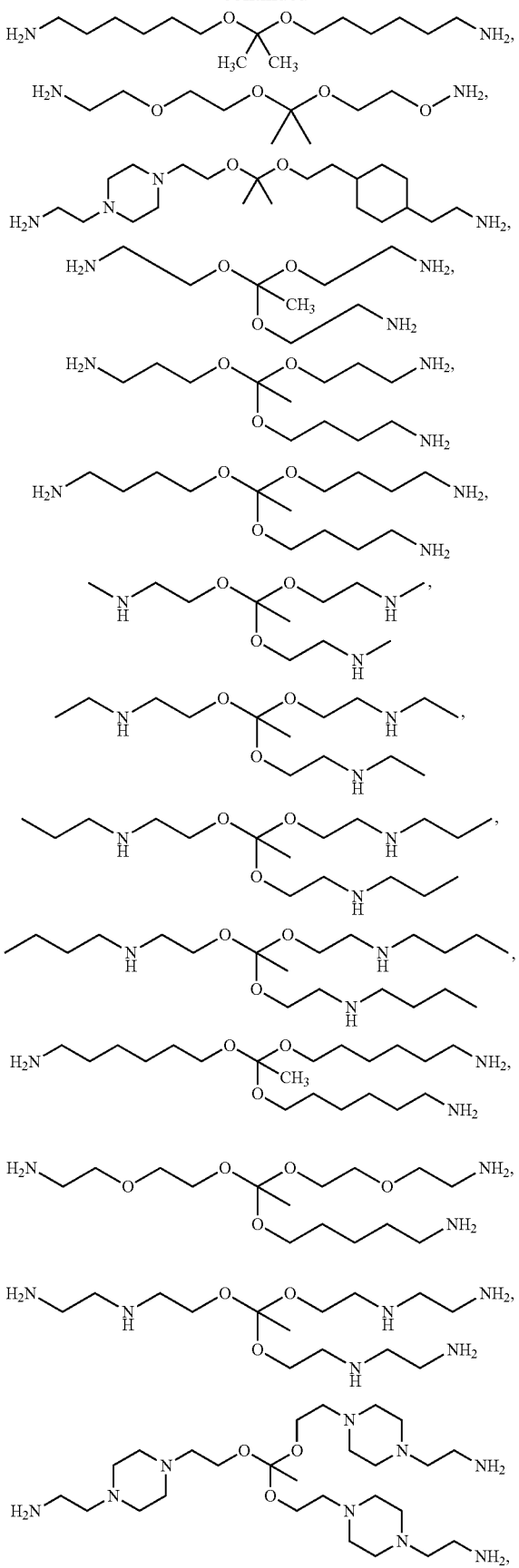

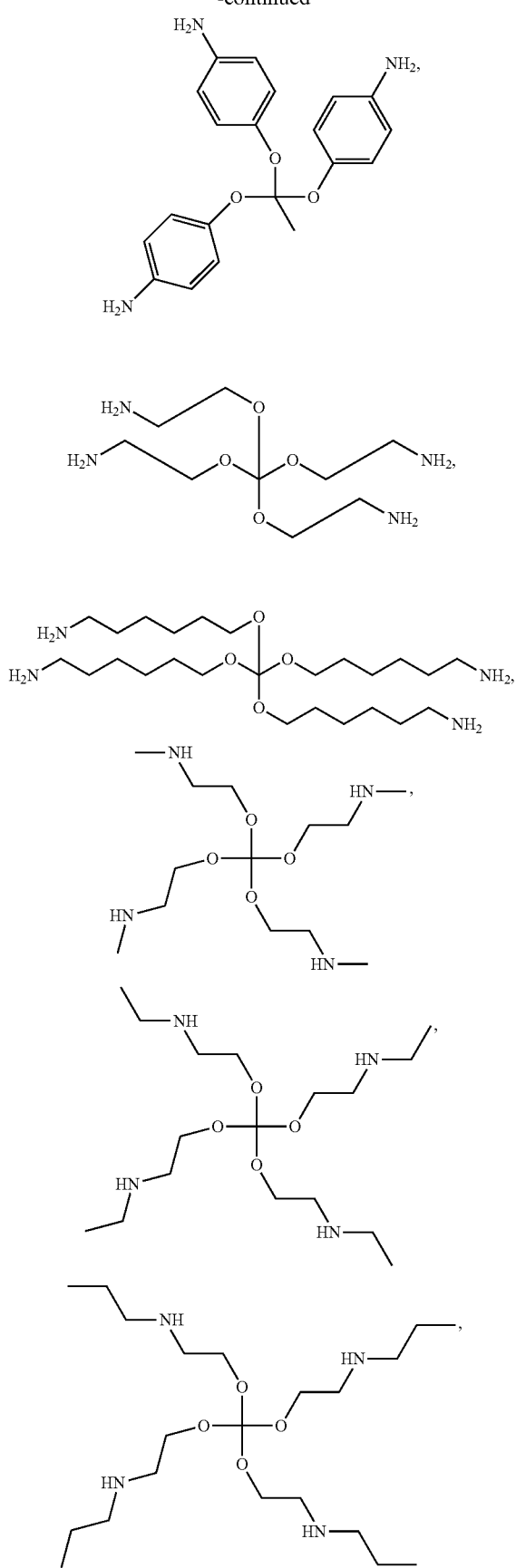

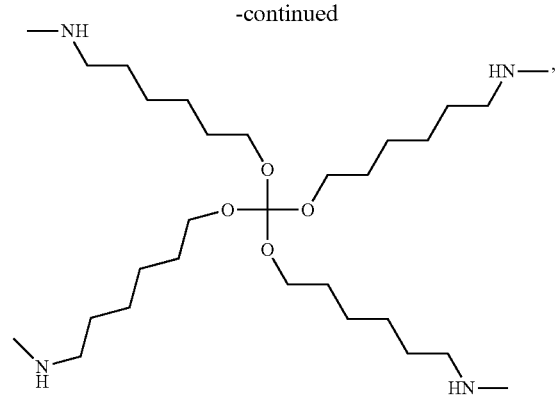
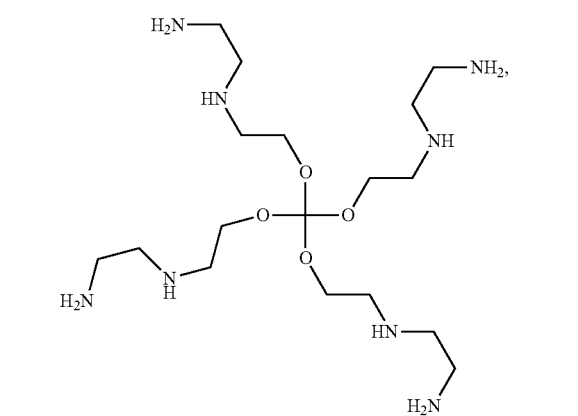
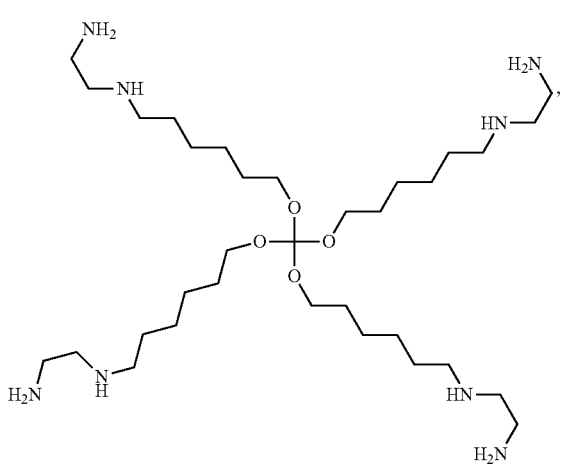
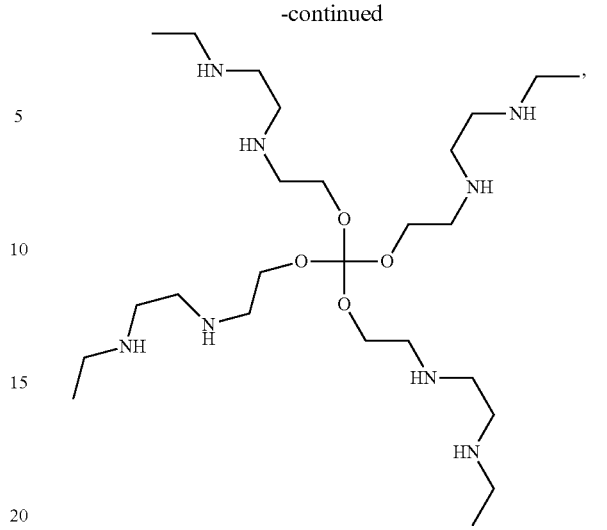
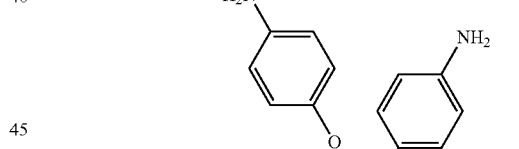
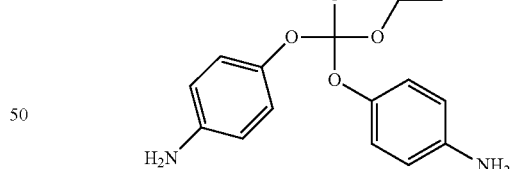
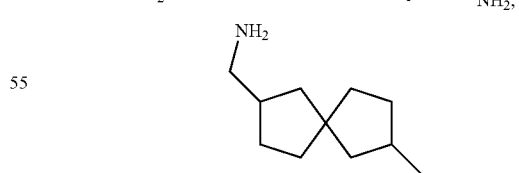
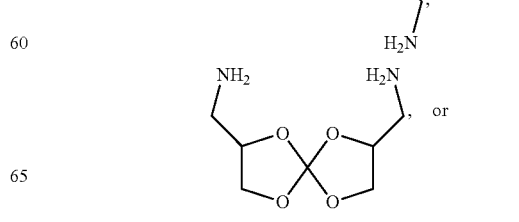

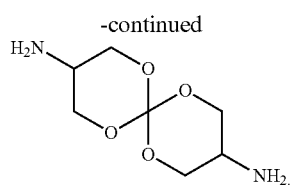

18. The epoxy matrix of claim 14, wherein the compound is:

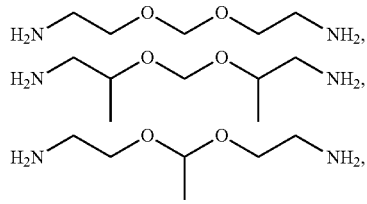

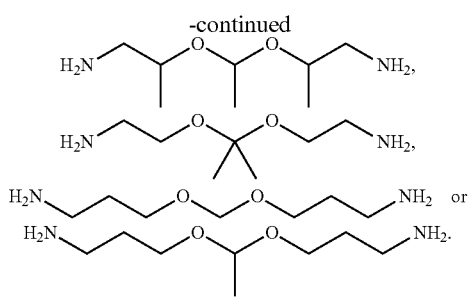

19. A method of recycling a cross-linked polymer, comprising:
(a) degrading the cross-linked polymer under an acidic condition into smaller, soluble molecules and/or polymers;
(b) and removing the degraded the cross-linked polymer, wherein the cross-linked polymer comprises cleavable links derived from an acid-labile cross-linking agent comprising a compound selected from:

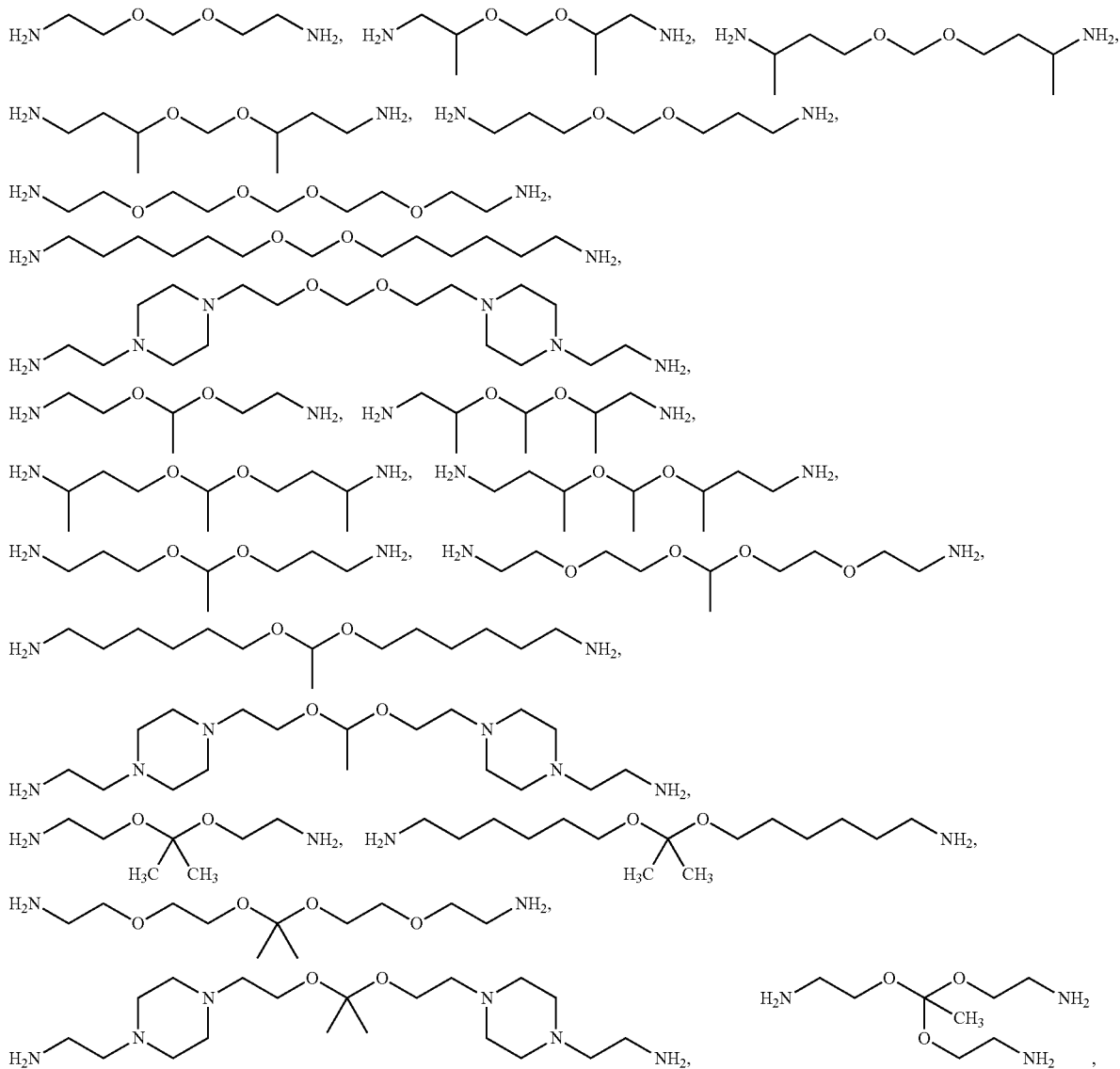

-continued
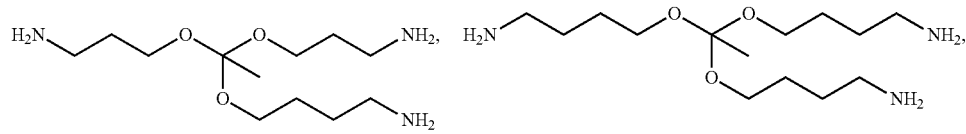
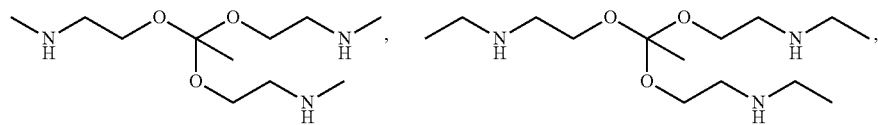
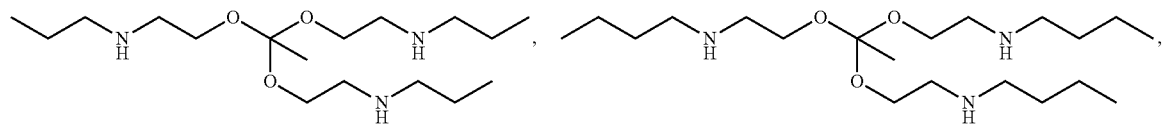
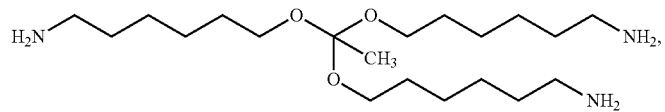
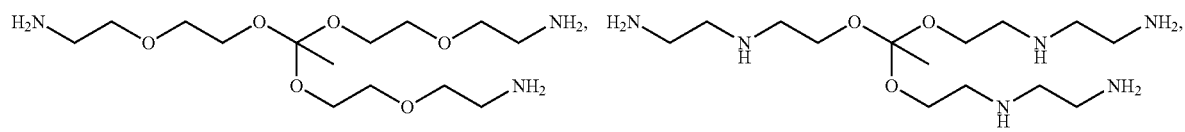
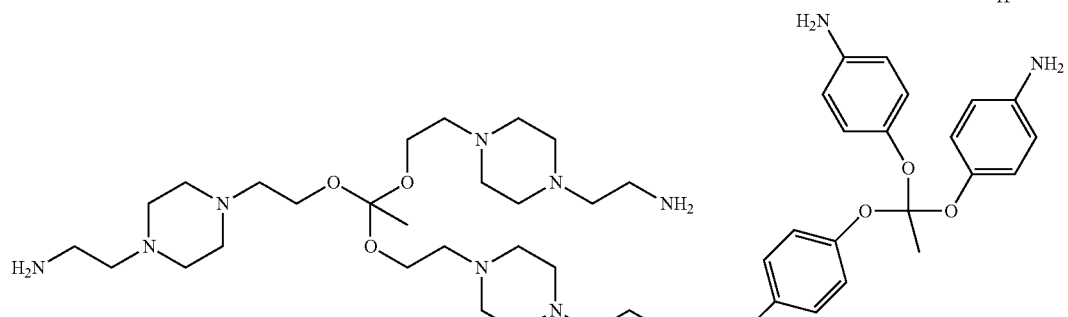
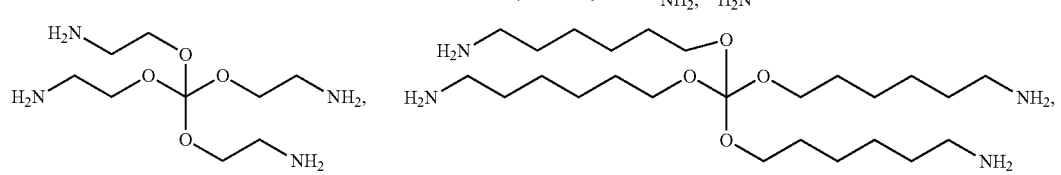
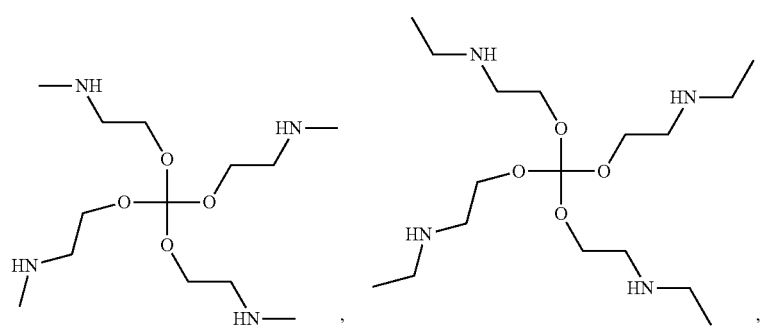

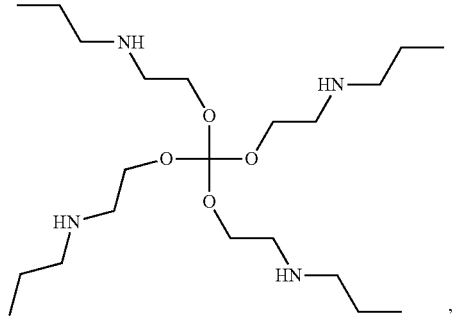 [SMILES: CCCNCCOC(OCCNCCC)(OCCNCCC)OCCNCCC]
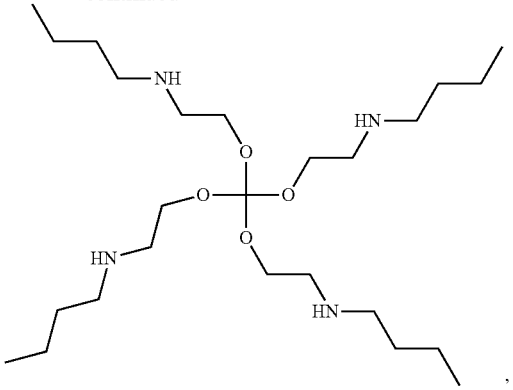
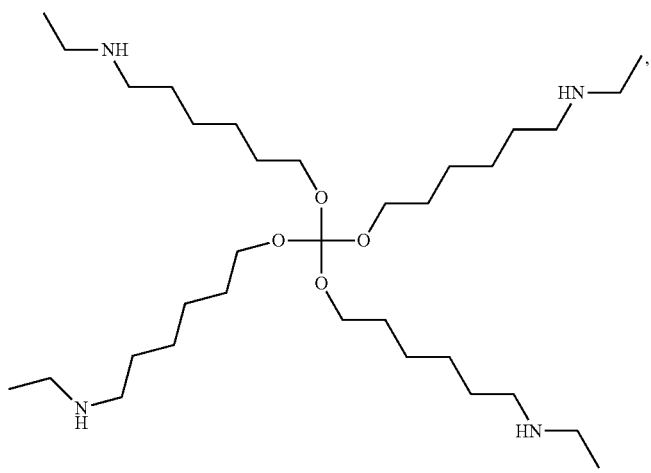
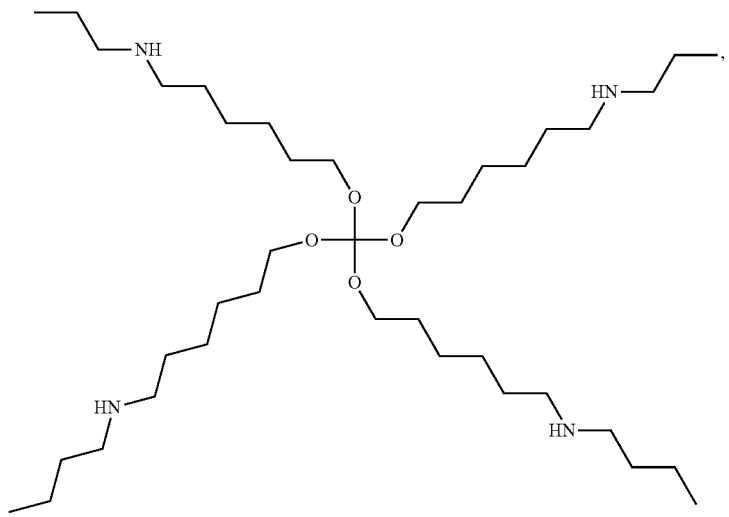

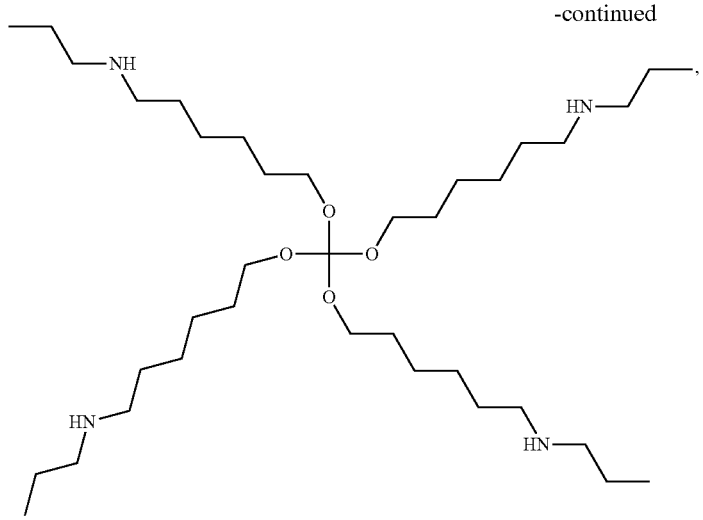
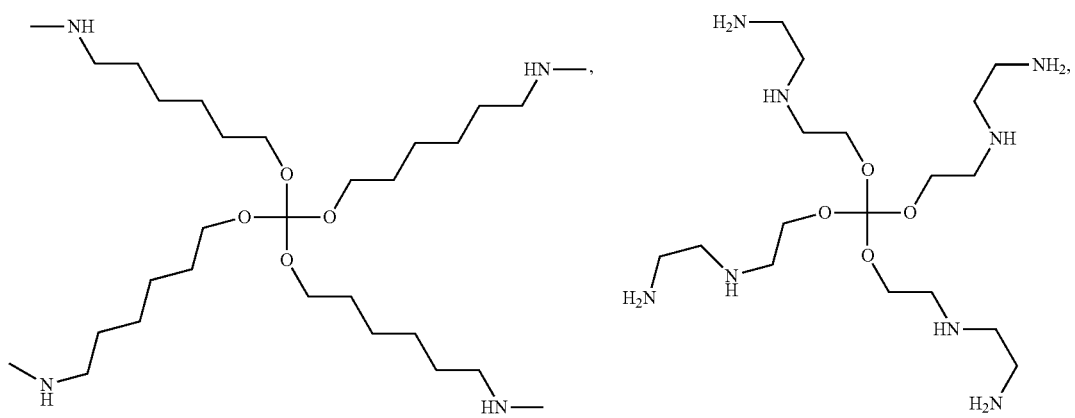
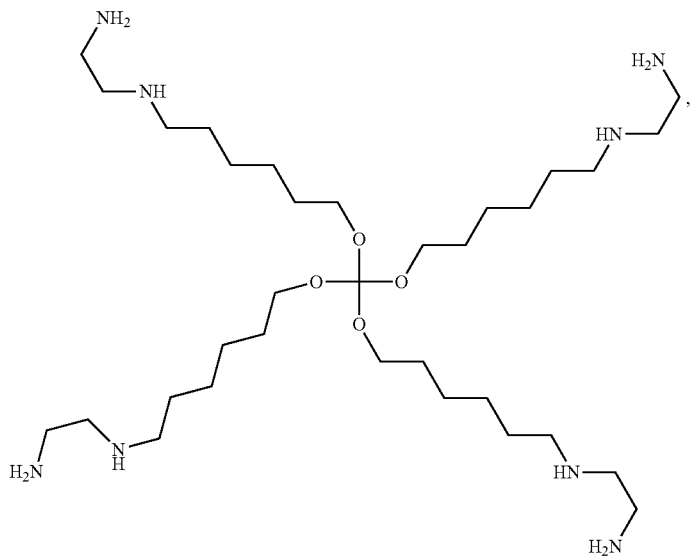

-continued
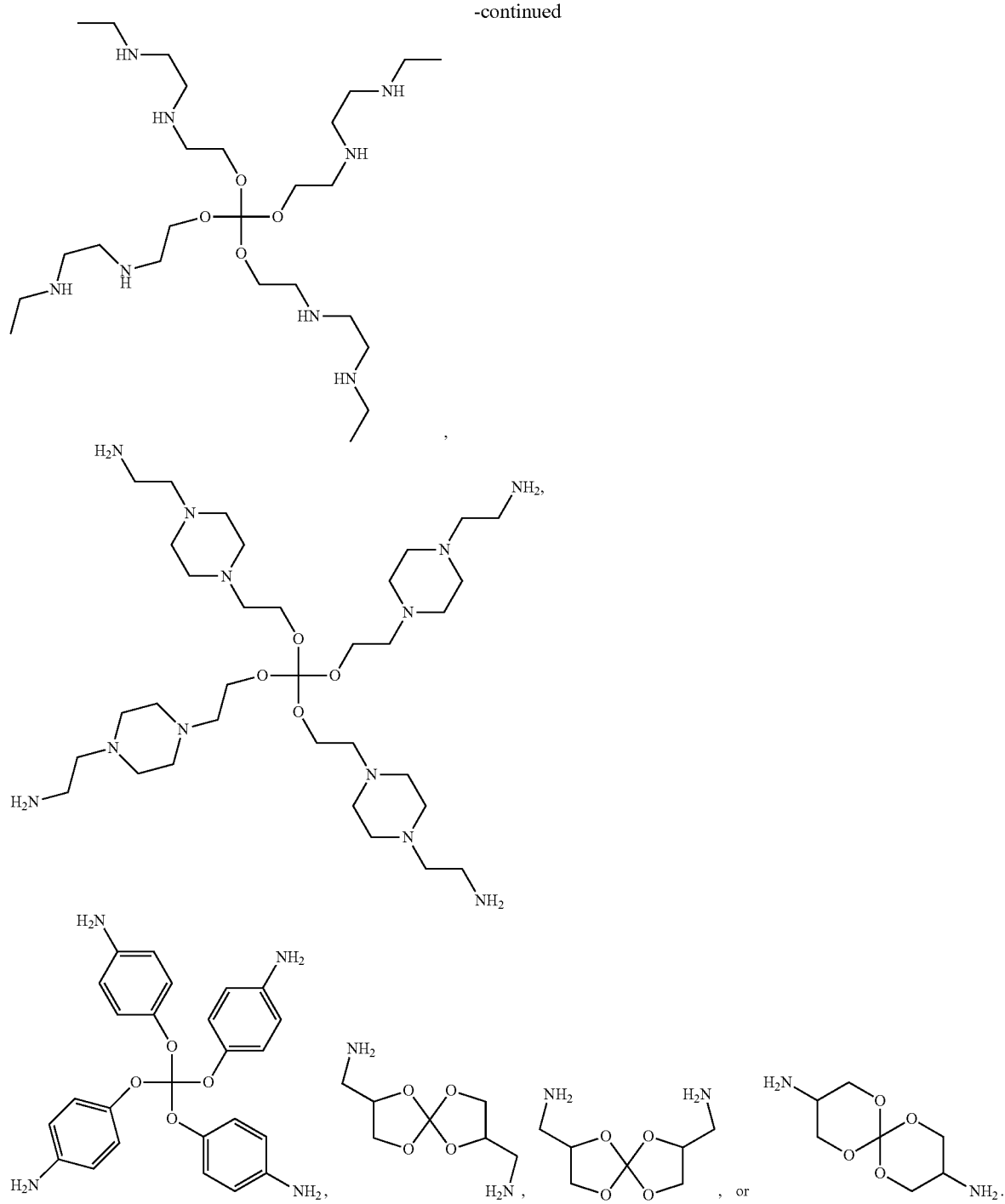
20. The method of claim 19, wherein $R^1$ is independently hydrogen, alkyl, or aryl.
21. The method of claim 19, wherein $R^1$ is independently hydrogen or methyl.
22. The method of claim 19, wherein the compound is:
-continued
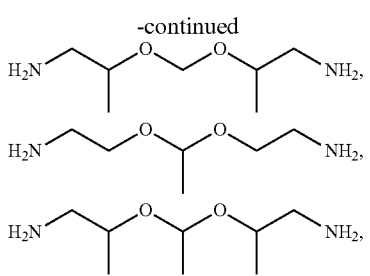

-continued
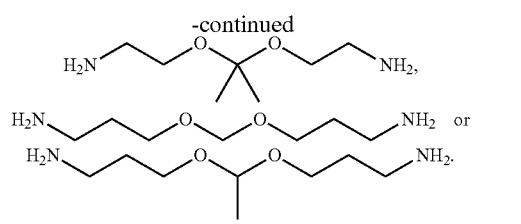
* * * * *